United States Patent
Healy

(10) Patent No.: US 10,522,243 B2
(45) Date of Patent: Dec. 31, 2019

(54) SPARSE IDENTITY SPACES IN DROPLET SEQUENCING

(71) Applicant: Bio-Rad Laboratories, Inc., Hercules, CA (US)

(72) Inventor: John Healy, Acton, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 364 days.

(21) Appl. No.: 15/353,625

(22) Filed: Nov. 16, 2016

(65) Prior Publication Data
US 2017/0147746 A1    May 25, 2017

Related U.S. Application Data

(60) Provisional application No. 62/258,370, filed on Nov. 20, 2015.

(51) Int. Cl.
*G16B 30/00*    (2019.01)
*C12Q 1/6869*   (2018.01)
*C12Q 1/6874*   (2018.01)

(52) U.S. Cl.
CPC ........... *G16B 30/00* (2019.02); *C12Q 1/6869* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 5,525,464 A * | 6/1996 | Drmanac | C12Q 1/6827 435/6.1 |
| 2002/0102567 A1 | 8/2002 | Fodor et al. | |
| 2012/0021423 A1 * | 1/2012 | Colston, Jr. | B01F 3/0807 435/6.12 |

(Continued)

FOREIGN PATENT DOCUMENTS

| | | | | |
|---|---|---|---|---|
| CN | 101240341 B | 6/2010 | | |
| WO | WO-2014043388 A1 * | 3/2014 | ........ | B01L 3/502784 |

(Continued)

OTHER PUBLICATIONS

Bio-Rad Laboratories, Inc. QX200™ Droplet Reader and QuantaSoft™ Software Instruction Manual. 2013.*

(Continued)

*Primary Examiner* — Soren Harward
(74) *Attorney, Agent, or Firm* — Kilpatrick Townsend and Stockton LLP

(57) ABSTRACT

A method for determining a sequence of a target nucleic acid is described. The method uses a plurality of control oligonucleotides with known sequence and unique identifications to map hybridization signals associated with a plurality of sequencing probes to a loosely packed multi-dimensional dye space, such that a region in the dye space can be associated with one or more sequencing probes. When a detected target hybridization signal of a sequencing probe and a target nucleic acid is mapped to the multi-dimensional dye space, the sequencing probe and thus the corresponding nucleotides in the target nucleic acid can be determined based on the one or more sequencing probes associated with the region that the detected target hybridization signal is mapped to.

7 Claims, 28 Drawing Sheets

Specification includes a Sequence Listing.

(56) References Cited

U.S. PATENT DOCUMENTS

2013/0084572 A1* 4/2013 Hindson ............ G01N 21/6428
435/6.12
2015/0024945 A1 1/2015 Healy
2015/0169824 A1* 6/2015 Kermani ................. G06F 19/24
702/19

FOREIGN PATENT DOCUMENTS

WO 2014/144491 A1 9/2014
WO 2015/095066 A1 6/2015

OTHER PUBLICATIONS

Frank, E., Hall, M. & Pfahringer, B. Locally Weighted Naive Bayes. in Uncertainty in Artificial Intelligence 249-256 (Morgan Kaufmann Publishers Inc., 2003).*
Mazaika, E. & Homsy, J. Digital Droplet PCR: CNV Analysis and Other Applications. Current Protocols in Human Genetics 82, 7.24.1-7.24.13 (2014).*
Acuña, E. & Rodriguez, C. The Treatment of Missing Values and its Effect on Classifier Accuracy. in Classification, Clustering, and Data Mining Applications 639-647 (2010).*
International Search Report and Written Opinion in PCT Application No. PCT/US2016/062333; dated Jan. 30, 2017; 12 pages.
Ben-Dor A. et al.; "On the Complexity of Positional Sequencing by Hybridization"; *Journal of Computational Biology*,vol. 8, No. 4; Sep. 1, 2001; pp. 361-371.
Extended European Search Report from EP Application dated Jul. 23, 2019; 6 pages.
Abate, A.R. et al.; "DNA sequence analysis with droplet-based microfluidics"; Lab On A Chip; vol. 13, No. 24; Jan. 1, 2013; pp. 4864-4869.

* cited by examiner

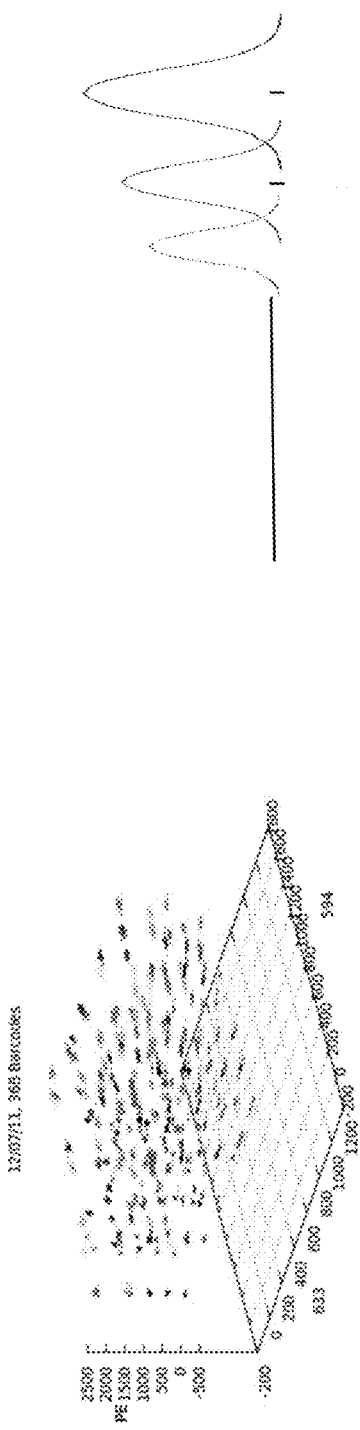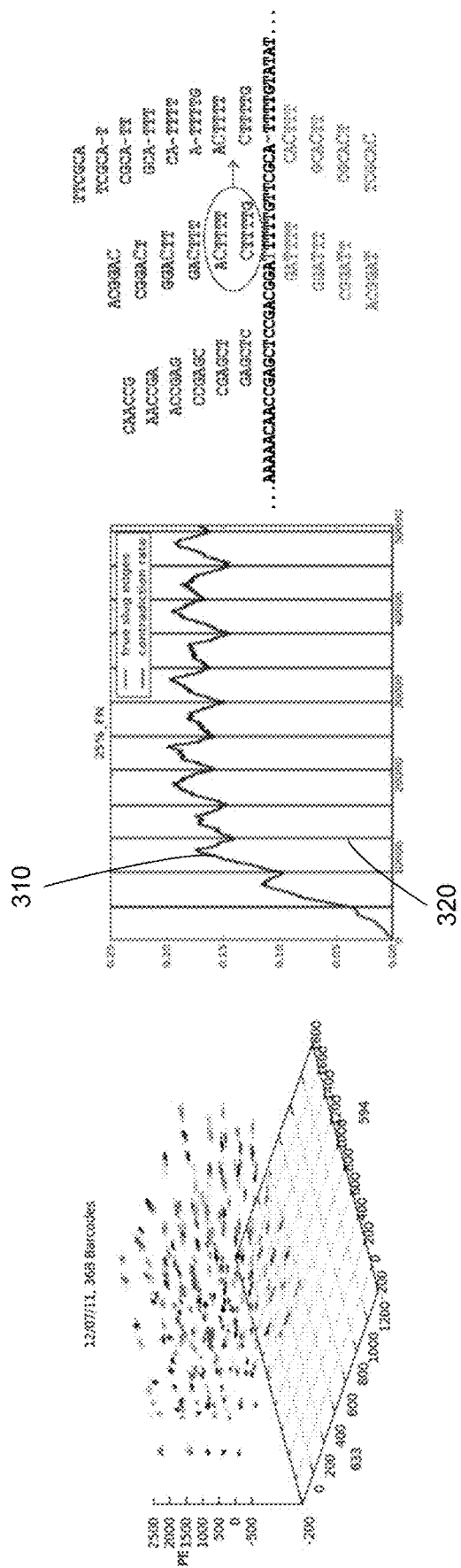
FIG. 3A
FIG. 3B
FIG. 3C
FIG. 3D
FIG. 3E

| Control Oligo ID | First Control Marker Probe | Second Control Marker Probe | Third Control Marker Probe |
|---|---|---|---|
| 1 | 1 | 5 | 8 |
| 2 | 1 | 8 | 13 |
| ... | ... | ... | ... |
| 400 | 11 | 14 | 15 |

FIG. 9

| Control Oligo ID's | 1 | 2 | 3 | 4 | 5 | 6 | 7 | 8 | 9 | 10 | ... | 400 |
|---|---|---|---|---|---|---|---|---|---|---|---|---|
| 1 AGTCAG | 1 | 0 | 0 | 0 | 1 | 1 | 0 | 0 | 1 | 1 | ... | 1 |
| 2 GGGGGT | 0 | 1 | 0 | 0 | 0 | 1 | 0 | 1 | 0 | 0 | ... | 0 |
| ... | | | | | | | | | | | | |
| 4096 | 0 | 1 | 0 | 1 | 0 | 0 | 0 | 1 | 0 | 0 | ... | 1 |

1010 points to the last cell of row 1 (value 0)
1020 points to a cell in row 4096 (value 0)

FIG. 10

SEQUENCE LISTING

```
<160> NUMBER OF SEQ ID NOS: 4

<210> SEQ ID NO 1
<211> LENGTH: 45
<212> TYPE: DNA
<213> ORGANISM: Artificial Sequence
<220> FEATURE:
<223> OTHER INFORMATION: synthetic - genomic DNA oligonucleotide

<400> SEQUENCE: 1
aaaaacaacc gagctccgac ggatttttgt tcgcattttg tatat            45

<210> SEQ ID NO 2
<211> LENGTH: 24
<212> TYPE: DNA
<213> ORGANISM: Artificial Sequence
<220> FEATURE:
<223> OTHER INFORMATION: synthetic 24-mer oligonucleotide

<400> SEQUENCE: 2
aggtgagtgg acccgtatat ggtt                                   24

<210> SEQ ID NO 3
<211> LENGTH: 18
<212> TYPE: DNA
<213> ORGANISM: Artificial Sequence
<220> FEATURE:
<223> OTHER INFORMATION: synthetic wild type reference oligonucleotide

<400> SEQUENCE: 3
```

```
aggcctgatt attacccc                                                    18

<210> SEQ ID NO 4
<211> LENGTH: 10
<212> TYPE: DNA
<213> ORGANISM: Artificial Sequence
<220> FEATURE:
<223> OTHER INFORMATION: synthetic decamer oligonucleotide

<400> SEQUENCE: 4
atcaggtctg                                                             10
```

SPARSE IDENTITY SPACES IN DROPLET SEQUENCING

CROSS-REFERENCES TO RELATED APPLICATIONS

The present application claims benefit of priority to U.S. Provisional Patent Application No. 62/258,370, filed Nov. 20, 2015, entitled "SPARSE IDENTITY SPACES IN DROPLET SEQUENCING," which is assigned to the assignee hereof and is incorporated herein by reference in its entirety for all purposes.

BACKGROUND

Deoxyribonucleic acid (DNA) sequencing is the process of determining the precise order of nucleotides within a DNA molecule, e.g., the order of the four bases—adenine, guanine, cytosine, and thymine—in a strand of DNA. Knowledge of DNA sequences has become useful for basic biological research, and in numerous applied fields such as diagnostic, biotechnology, forensic biology, and biological systematics. The rapid speed of sequencing attained with modern DNA sequencing technology has been instrumental in the sequencing of complete DNA sequences, or genomes of numerous types and species of life, including the human genome and other complete DNA sequences of many animal, plant, and microbial species. The advent of these rapid DNA sequencing methods has greatly accelerated biological and medical research and discovery.

Sequencing by hybridization (SBH) is a method of sequencing based on hybridization, or lack thereof, of a large number of different probe sequences to a target nucleic acid. By detecting hybridization of overlapping probes and absence of hybridization of probes of similar but different sequence, one can predict the nucleotide sequence of a target sequence.

However, due to noise, errors, or other imperfections in a sequencing system, the detected hybridization signals, when mapped to a dye space for assay calling, may be overlapped and densely packed, and thus are difficult to distinguish from each other for the correct identification of which probes hybridize with a given target nucleic acid.

BRIEF SUMMARY

Provided herein are methods for determining a nucleotide sequence of a target nucleic acid (e.g., a genomic region of an organism). In some embodiments, the method includes receiving a control hybridization signal indicating a hybridization of a sequencing probe from a plurality of sequencing probes with copies of respective control oligonucleotide in each control droplet of a plurality of control droplets from each control partition of a plurality of control partitions. Each control droplet of the plurality of control droplets includes copies of a respective control oligonucleotide of the plurality of control oligonucleotides. Each control oligonucleotide of the plurality of control oligonucleotides has a known sequence and a corresponding identification (ID).

The method further includes determining the identification (ID) of the control oligonucleotide in the control droplet for each control droplet of the plurality of control droplets of each control partition; mapping the control hybridization signal for each control droplet to a multi-dimensional control data point in a dye space; and storing the multi-dimensional control data point associated with the ID of the control oligonucleotide for each control droplet.

The method also includes, for each sequencing probe of the plurality of sequencing probes, obtaining a sequencing probe bit vector based on the known sequences of the plurality of control oligonucleotides, wherein each bit in the sequencing probe bit vector represents a presence or absence of the sequencing probe in a corresponding control oligonucleotide of the plurality of control oligonucleotides.

The method may also include receiving a first target hybridization signal for a first target droplet of a first target partition including copies of the target nucleic acid; mapping the first target hybridization signal to a first multi-dimensional target data point in the dye space; selecting a region in the dye space that includes the first multi-dimensional target data point; generating a region vector for the region, where each value in the region vector represents a contribution of any multi-dimensional control data points that are within the region and that have the ID of the corresponding control oligonucleotide; and identifying a first sequencing probe as hybridizing to the target nucleic acid based on a match condition between the region vector and the sequencing probe bit vector for the first sequencing probe.

Also provided herein is another method for determining a nucleotide sequence in a target nucleic acid. The method includes receiving, by an SBH system, a plurality of control partitions, where each control partition of the plurality of control partitions includes copies of a respective control oligonucleotide from a plurality of control oligonucleotides, and each control oligonucleotide of the plurality of control oligonucleotides has a known sequence and a corresponding identification (ID); and splitting each control partition of the plurality of control partitions into a plurality of control droplets, each control droplet including a plurality of copies of the control oligonucleotide for the control partition.

The method further includes detecting a control hybridization signal indicating a hybridization of a sequencing probe from a plurality of sequencing probes with copies of the control oligonucleotide in the control droplet for each control droplet in a first portion of the plurality of control droplets; determining the ID of the control oligonucleotide in each control droplet; mapping the control hybridization signal for each control droplet in the first portion of the plurality of control droplets to a multi-dimensional control data point in a dye space; and storing the multi-dimensional control data point associated with the ID of the respective control oligonucleotide.

The method also includes receiving or otherwise obtaining a sequencing probe bit vector based on the known sequences of the plurality of control oligonucleotides, wherein each bit in the sequencing probe bit vector represents a presence or absence of the sequencing probe in a corresponding control oligonucleotide of the plurality of control oligonucleotides.

The method may also include receiving a first target hybridization signal for a first target droplet of a first target partition including copies of the target nucleic acid, and mapping the first target hybridization signal to a first multi-dimensional target data point in the dye space; selecting a region in the dye space that includes the first multi-dimensional target data point; generating a region vector for the region, where each value in the region vector represents a contribution of any multi-dimensional control data points that are within the region and that have the ID of the corresponding control oligonucleotide; and identifying a first sequencing probe as hybridizing to the target nucleic acid based on a match condition between the region vector and a first sequencing probe bit vector for the first sequencing probe.

Alternatively, a region vector may be created for each region or each coherent region in the dye space. The region vector can be compared against the sequencing probe bit vector for each sequencing probe to determine one or more sequencing probes corresponding to each region. After the sequencing run or during the sequencing run, target hybridization signals of target droplets including copies of the target nucleic acids may be mapped to multi-dimensional target data points in the dye space. For each target data point in the dye space, one or more sequencing probes may be associated with the target data point based on the one or more sequencing probes corresponding to the region that the target data point falls into in the dye space.

Other aspects of the invention are described as well, including a microfluidic system that can be used to perform the methods described herein, and a computer product including a computer-readable medium storing instructions for causing a system to perform the methods described herein.

DEFINITIONS

The term "nucleic acid amplification" or "amplification reaction" refers to any in vitro means for multiplying copies of a target sequence of nucleic acid. Such methods include but are not limited to polymerase chain reaction (PCR), deoxyribonucleic acid (DNA) ligase chain reaction (LCR) (see, e.g., U.S. Pat. Nos. 4,683,195 and 4,683,202; PCR Protocols: A Guide to Methods and Applications (Innis et al., eds, 1990)), QBeta ribonucleic acid (RNA) replicase, and RNA transcription-based amplification reactions, such as Trans-acting siRNA (TAS) and self-sustained sequence replication (3 SR), as well as others known to those of skill in the art.

"Amplifying" refers to a step of submitting a solution to conditions sufficient to allow for amplification of a polynucleotide. Components of an amplification reaction include, e.g., primers, a polynucleotide template, polymerase, nucleotides, and the like. The term amplifying typically refers to an "exponential" increase in target nucleic acid. However, amplifying as used herein can also refer to linear increases in the numbers of a select target sequence of nucleic acid, such as is obtained with cycle sequencing.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step. PCR can be performed as end-point PCR (i.e., only monitored at an end point) or as quantitative PCR (monitored in "real time").

A "primer" refers to a polynucleotide sequence that hybridizes to a sequence on a target nucleic acid and serves as a point of initiation of nucleic acid synthesis. Primers can be of a variety of lengths but are less than 50 nucleotides in length, for example 5-30 nucleotides, in length. The length and sequences of primers for use in PCR can be designed based on principles known to those of skill in the art, see, e.g., Innis et al., supra.

A "template" refers to a polynucleotide sequence that comprises the polynucleotide to be amplified, flanked by or a pair of primer hybridization sites. Thus, a "target template" comprises the target polynucleotide sequence flanked by hybridization sites for a "forward" primer and a "reverse" primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga maritime*, or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.). Polymerases include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

The terms "label," "detectable label," "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, $^{32}P$ and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating a label to a desired agent may be employed, e.g., using methods described in Hermanson, *Bioconjugate Techniques* 1996, Academic Press, Inc., San Diego.

As used herein, the term "partitioning" or "partitioned" refers to separating a sample into a plurality of portions, or "partitions." Partitions can be solid or fluid. In some embodiments, a partition is a solid partition, e.g., a microchannel. In some embodiments, a partition is a fluid partition, e.g., a drop. In some embodiments, a fluid partition (e.g., a drop) is a mixture of immiscible fluids (e.g., water and oil). In some embodiments, a fluid partition (e.g., a droplet) is an aqueous droplet that is surrounded by an immiscible carrier fluid (e.g., oil).

As used herein, a "slug" refers to a partition comprising target nucleic acids or control oligonucleotides.

BRIEF DESCRIPTION OF THE DRAWINGS

FIG. 3A illustrates examples of designed sequencing probes with different dyes and different intensities of each dye assigned to each sequencing probe, represented in a three-dimensional dye space.

FIG. 3B illustrates a waveform of detected hybridization signal.

FIG. 3C is a scatter plot showing assay intensity data from a sequencing experiment.

FIG. 3D is a plot showing edges of target nucleic acid partitions according to embodiments of the present invention.

FIG. 3E illustrates an example of sequence assembly (genomic DNA=SEQ ID NO:1) based on the presence or absence of hybridization of sequencing probes.

FIG. 9 illustrates an example table for encoding the control oligonucleotide ID using three different control marker probes.

FIG. 10 illustrates examples of sequencing probe bit vectors.

FIG. 22A illustrates data points of 4096 clusters in the same color. FIG. 22B illustrates data points of 4096 clusters in different colors. FIG. 22C is a zoom-in view of FIG. 22B.

FIG. 23A illustrates data points of 4096 clusters in the same color. FIG. 23B illustrates data points of 4096 clusters in different colors. FIG. 23C is a zoom-in view of FIG. 23B.

DETAILED DESCRIPTION

Provided herein are methods for determining a nucleotide sequence of a target nucleic acid based on hybridization of sequencing probes to the target nucleic acid. Control oligonucleotides with known sequences may be sequenced using the sequencing probes to provide control data points that can be used as references to determine which sequencing probes have hybridized with the target nucleic acid in a given droplet. In this manner, at least some noise and errors in the sequencing process may be reduced. Using the control data points from the control oligonucleotides and the known sequences of the control oligonucleotides, regions in a dye space where the control data points are mapped to may be associated with one or more sequencing probes. When a target hybridization signal of a sequencing probe hybridized with the target nucleic acid is mapped into a target data point in a region in the dye space, the target data point can be associated with the one or more sequencing probes assigned to the region. Thus, it can be determined that the target nucleic acid may hybridize with the one or more sequencing probes assigned to the region. The sequence of the target nucleic acid can then be assembled based on the sequences of all sequencing probes that can hybridize with the target nucleic acid.

Also provided herein are systems and computer products for performing the methods described herein.

I. Sequencing by Hybridization

The methods described herein rely on hybridizations, or lack thereof, of a large number of different sequencing probes to a target nucleic acid. The basic idea behind sequencing by hybridization (SBH) is that sequences of a nucleic acid can be obtained by the maximal and unique overlap of their constituent oligomers. For example, three octamers ATCAGGTC, TCAGGTCT, and CAGGTCTG may uniquely define a decamer ATCAGGTCTG (SEQ ID NO:4). Thus, no knowledge of the frequency or the position of the oligomers is used for determining the sequence because the knowledge of oligomer sequences and hybridization results may be sufficient for determining the sequence.

The target nucleic acid to be sequenced may be generated in partitions, for example, with a PCR reaction. Partitions including nucleic acids to be sequenced may be referred to herein as "slugs." By detecting the hybridization of overlapping sequencing probes with the target nucleic acid and the lack of hybridization of other sequencing probes of similar but different sequence with the target nucleic acid, one can predict the nucleotide sequence of a target partition of a nucleic acid or the target nucleic acid. More details of the sequencing by hybridization (SBH) can be found in U.S. patent application Ser. No. 14/290,867, filed on May 29, 2014, entitled "SYSTEMS AND METHODS FOR SEQUENCING IN EMULSION BASED MICROFLUIDICS," which is incorporated herein by reference for all purposes.

A. System

Figure 1:
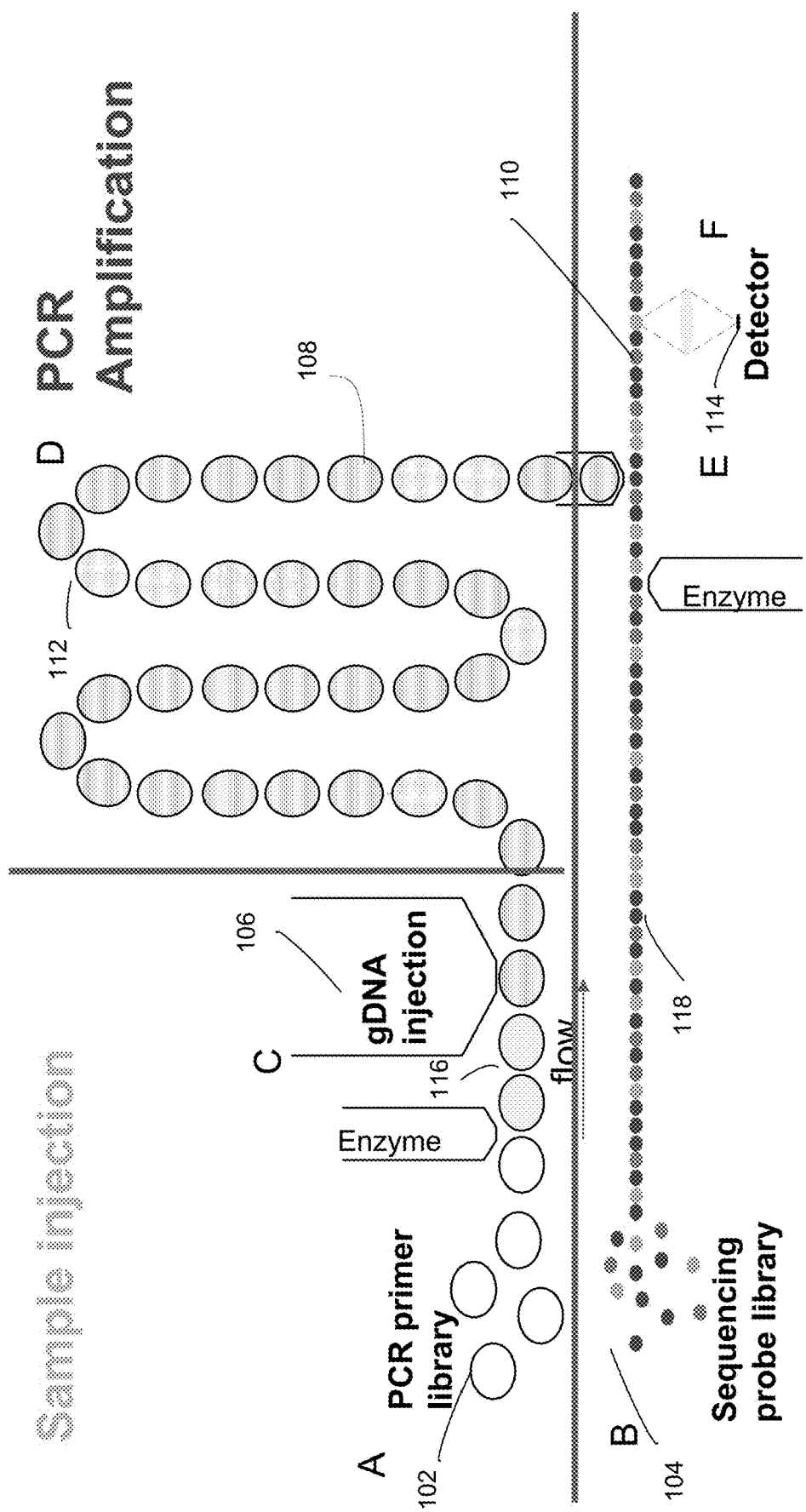
FIG. 1 is a schematic of a microfluidic device used in sequencing by hybridization.

FIG. 1 is a schematic of a microfluidic system 100 for serialized pipelined sequencing by hybridization (SBH). Microfluidic system 100 includes two reservoirs that can be preloaded with emulsified reagents. Reservoir A contains emulsified reagents for performing a PCR reaction, including at least one PCR primer pair and other PCR reagents, such as polymerases. Reservoir B contains emulsified reagents for the sequencing, the reagents including at least one sequencing probe. Microfluidic system 100 also includes two microfluidic channels 116 and 118. Microfluidic channel 116 is coupled to reservoir A, and microfluidic channel 118 is coupled to reservoir B.

Injection point C is where a small portion of genomic DNA sample or other oligonucleotides, such as reference or control oligonucleotides, is injected into each of a plurality of PCR partitions or slugs 108. Section D includes a serpentine channel 112 where PCR amplification may be performed. Serpentine channel 112 in section D may include at least two distinct thermal zones and can act as an online thermal cycler. Each of PCR partitions or slugs 108 flows through serpentine channel 112 and is amplified in serpentine channel 112. The amplification reaction may also introduce a fluorescent molecule to the 5' end of a target partition of the genomic DNA sample.

From serpentine channel 112, each amplified PCR partition or slug 108 reaches a second injection point E, where each amplified PCR partition or slug 108 may be injected into a series of droplets comprising different sequencing probes to form a series of reaction droplets 110. The sequencing probe may include one or more different dyes at one of several possible concentrations, such that the concentration of the different dyes indicates the identities of the sequencing probes. The series of reaction droplets 110 may flow downstream of injection point E to an optical detector 114 at point F. Optical detector 114 at point F can read a fluorescent signal from each reaction droplet that flows by optical detector 114.

In some embodiments, all of the above described components may be provided as part of a single cartridge. In some embodiments, the cartridge can in turn be inserted into a manifold allowing for attachment to one or more pumps configured to pump drops through the microfluidic channels.

In some embodiments, all components of the systems and methods described herein are microfluidic. "Microfluidic," as used herein, may refer to a device, apparatus or system including at least one fluid channel having a cross-sectional dimension of less than 1 mm, and a ratio of length to largest cross-sectional dimension perpendicular to the channel of at least about 3:1. A "microfluidic channel," as used herein, is a channel meeting these criteria.

1. Target Partitions of a Genomic DNA Sample

Partitions comprising appropriate primers to amplify the target nucleic acid can be combined with partitions of template polynucleotides, such as, for example, sample genomic DNA, cDNA, mitochondrial DNA, and RNA, and submitted to thermocyclic conditions for a number of cycles such as 5, 10, 15, 20, 25, 30, or more, to generate an amplicon. As shown in FIG. 1, one way to submit partitions or slugs 108 to thermocyclic conditions is to pass partitions or slugs 108 through microfluidic serpentine channel 112, where different regions of serpentine channel 112 are exposed to different temperatures, such as, for example, a primer extension temperature and a primer annealing temperature, of a thermocyclic reaction.

Target nucleic acids can be any natural or synthetic nucleic acids that can be involved in "Watson-Crick" base pairing. In many embodiments, the target nucleic acids are DNAs or RNAs. The target nucleic acids can be derived from any organism. In some embodiments, target nucleic acids obtained from one or more eukaryotic or prokaryotic cells can be used in the present invention. In some embodiments, the cells are animal cells, including but not limited to, human, or non-human, mammalian cells. Non-human mammalian cells include but are not limited to, primate cells, mouse cells, rat cells, porcine cells, and bovine cells. In some embodiments, the cells may be non-mammalian cells, such as avian, reptilian, or other cells. In some embodiments, the cells may be plant cells. The cells can be, for example, cultured primary cells or immortalized culture cells, or can be from a biopsy or tissue sample, optionally cultured and stimulated to divide before assayed. In some embodiments, the cells can be from a tumor biopsy or other diseased tissue.

The target nucleic acids can be double- or single-stranded. The target nucleic acids can be of any length as desired. Generally, longer target nucleic acids will require more complex deconvolution due to an increased number of logical alternatives that need to be resolved. In some embodiments, the target nucleic acid is 50-1000 base pair (bp), 100-500 bp, or 100-250 bp long. In some embodiments, the target nucleic acid may be an amplicon, for example, generated by amplification.

In some embodiments, the target nucleic acid comprises, or is a portion of, a genetic biomarker for a disease, prognosis, or indication. As an example, in some embodiments, the target nucleic acid's genotype is associated with a particular cancer or diabetes phenotype. In some embodiments, the biomarker is useful for predicting responsiveness to a drug for treating an indication, including but not limited to, cancer.

2. Sequencing Probes

A sequencing probe library can be provided in reservoir B of FIG. 1. As an example, a library of contiguous (or gapped) hexamers of all possible sequences (4096) can be provided. The sequencing probes may further comprise one or more different dyes at one of several possible concentrations, such as four different dyes each at one of eight possible concentrations, which gives a total of 4096 different combinations. A series of droplets may be generated from the sequencing probe library in reservoir B, each including copies of a sequencing probe. Small portions of target nucleic acid partitions or slugs 108 can be injected into the series of droplets to form reaction droplets. Each target nucleic acid partitions or slugs 108 can be injected into many reaction droplets, such as hundreds, thousands, or more. A strand displacement polymerase may be added to the sequencing probes before or after they are merged with the target nucleic acid partitions in the reaction droplets.

The number of different sequencing probes used to determine a target nucleic acid sequence may be a function of the length and complexity of the target nucleic acid, and the number of nucleotides in each sequencing probe.

Much attention has been given to the optimal selection of sequencing probes, their combined sequence complexity, and the optimal surface conditions, in an effort to maximize hybridization signals as well as to maximize the resolvable size of target molecules. Information and knowledge in these fields can be applied to embodiments of the present invention. See, e.g., R. Drmanac, et al., Science 260:1649-1652 (1993); R. Drmanac, et al., J. Biomol. Struct. Dyn. 5: 1085 (1991); PEVZNER, et al., J. BIOMOLECULAR STRUCTURE & DYNAMICS 9(2): 399-410 (1991); B. HUDSON: "An Experimental Study of SBH with Gapped Probes" TECHNICAL REPORT CS-99-07, DEPT. OF COMPUTER SCIENCE, BROWN UNIVERSITY, April 1999; and PCT Patent Publication No. WO 2000/022171.

Sequencing probes as described herein may include additional markers to identify reagents, for example, oligomers, within a particular sequencing probe. For example, in some embodiments, one or more marker reagents can be inserted into each different sequencing probe such that each sequencing probe is represented by a pre-determined and known unique signal based on the one or more marker reagents in the sequencing probe. By allowing for a unique detectable characteristic for each sequencing probe, one can thereby determine which sequencing probe resulted in hybridization. For example, in some embodiments, the presence/absence of hybridization and the marker characteristic can be detected for each reaction droplet, with the marker characteristic indicating the identity of the sequencing probes in the reaction droplets.

In some embodiments, the marker characteristic can be generated by the presence of one or more spectroscopic substance. For example, the spectroscopic substance may comprise one or more selectively absorbent molecules. A "selectively absorbent molecule," as used herein, refers to a molecule that absorbs certain characteristic colors or wavelengths of light while allowing other colors or wavelengths of light to pass or transmit through the molecule when a broadband light source is directed at the molecule. One of skill in the art will know and appreciate the numerous selectively absorbent molecules that may be used as the selectively absorbent substance/constituent according to the present invention, including but not limited to, those commercially available from Exciton (Dayton, Ohio) and QCR Solutions, Corp. (Port St. Lucie, Fla.).

In some embodiments, the spectroscopic substance comprises one or more fluorescent molecule or fluorescent moiety. A "fluorescent molecule" or "fluorescent moiety," as used herein, refers to a "fluorescent material," "fluorescent label," "fluorophore," or "fluorescent dye", each of which as used herein may be a fluorescent molecule, a fluorescent semiconductor nanoparticle ("quantum dot"), or a chelated lanthanide or lanthanoid, capable of absorbing energy from light of a specific wavelength, and then emitting the absorbed energy as fluorescence having another specific wavelength characteristic for the particular molecule or quantum dot. In this way, the fluorophore facilitates the final assay readout indicating the presence or absence of a particular target sequence of interest in the sample.

3. Droplets Injection

In various embodiments, the system further comprises one or more droplet injectors. In some embodiments, the system, such as microfluidic system 100 of FIG. 1, includes two droplet injectors. A first droplet injector is located in a first microfluidic channel, such as microfluidic channels 116 of FIG. 1, and is configured to inject partitions of nucleic acids from sample nucleic acid into droplets comprising PCR primer pairs from, for example, reservoir A of FIG. 1, to form target nucleic acid partitions. A second droplet injector is configured to inject portions of the target nucleic acid partitions in the first microfluidic channel into sequencing probe droplets that travel down a second microfluidic channel, such as microfluidic channels 118 of FIG. 1, to form a series of reaction droplets. Droplet injectors are described in, for example, U.S. Pat. Publication No. 2012/0132288.

In some embodiments, a target nucleic acid partition may be divided into at least 50, 100, 200, 300, 400 or more (e.g., 50-1000, 50-500, 50-5000) portions, where each portion is then injected into and mixed with a different sequencing probe droplet to form a series of reaction droplets. Note that while it is desirable to combine each portion of the target nucleic acid partition with a different type of sequencing probe, this may not be required to obtain an accurate sequence. It may be common in various embodiments that 5%, 10%, 20% or more sequencing probes in a sequencing probe set do not react with the target nucleic acid.

Dyes may be incorporated into each reaction droplet, either at the time of droplet formation or after the droplet formation using any injection method known to one of skill in the art. Dyes may be incorporated during droplet formation by flowing or streaming the desired dye composition as a fluid stream into a droplet-maker design. Droplet-making designs and methods include but are not limited to those described in International Patent Publications WO 2004/002627 and WO 2006/096571, each of which is incorporated herein in its entirety.

Microfluidic systems may be configured to cause two or more droplets to fuse or coalesce into one droplet, for example, in cases where the two or more droplets ordinarily are unable to fuse or coalesce due to, for example, composition, surface tension, droplet size, etc. as known to those of ordinary skill in the art. The fluidic droplets may be fused together using any suitable technique, for example, as described in U.S. Patent Application Publication No. 2006/0163385, or U.S. Patent Application Publication No. 2007/0003442, each of which is incorporated herein by reference. As an example, in microfluidic systems, the surface tension of the droplets may prevent fusion or coalescence of the droplets from occurring. In one embodiment, two droplets may be given opposite electrical charges (i.e., positive and negative charges, but not necessarily of the same magnitude), which may increase the electrical interaction of the two droplets such that fusion or coalescence of the droplets can occur. Electrical charges (positive or negative) may be imparted onto droplets through the use of Taylor cones, or through any other suitable techniques. For instance, an electric field may be imposed on a reactor containing the droplets, the droplets may pass through a capacitor, and a chemical reaction may occur to cause the droplets to become charged.

4. Reaction Droplets Detection

The reaction droplets, comprising a displacing polymerase and a hybridizing quencher polynucleotide, may proceed through a microfluidic channel under conditions allowing for displacement of the quencher polynucleotide if at least one of the sequencing probes hybridizes to the target nucleic acid.

Signals from the reaction droplets can be detected continuously by one or more detector such as detector 114 in FIG. 1. The detected signals may indicate the presence, absence, or differential levels of fluorescence from the fluorescent molecule in the reaction droplets, thereby determining the presence or absence of hybridization of different sequencing probes with the target nucleic acid. The detected signals may also indicate the level and identity of various dyes in the droplets, thereby identifying the particular sequencing probe in each droplet.

Detectors as described herein can detect one or both of the signals from the hybridization assay or the dyes in the sequencing probe for identifying the sequencing probe. In some embodiments, the droplets in an emulsion flow through microfluidic channels, passing an optical detector that measures a fluorescent signal coming from the droplets. In some embodiments, multiple sets of measurements of the same target nucleic acid over time can be generated and aggregated.

The detectors may also measure the spectroscopic intensity and wavelength of a spectroscopic substance using any method for spectroscopic analysis known and appreciated by one or ordinary skill in the art. Spectroscopic methods that may be utilized in the present invention include, but are not limited to, a laser and photodetector pair system or more complex optics known to those of skill in the art where the path of an optical beam intersects with the path of a spectroscopic substance and the excitation or illumination of the spectroscopic substance is captured by an optical system comprising one or more objective lens, mirror, and/or other optical components to direct the light to a photomultiplier tube (PMT) or photosensitive camera. As an example, by providing four different dyes at eight different dye concentrations, one can generate $8^4$ (or 4096) different unique identifiers in a dye space, each of which can be used to identify a unique sequencing probe.

The spectroscopic intensity measurements may comprise one or more methods, including but not limited to, light scatter, absorption, chemiluminescence, fluorescent intensity, radiation decay counts, colorimetric, and so forth. Samples to be tested can be placed in the path of an excitation energy source, such as a light source selected from, but not limited to, lasers, light-emitting diodes (LEDs), arc lamps, broadband light sources, and high intensity light bulbs. The spectroscopic substances in the sample to be tested may scatter, absorb, chemiluminesce, or fluoresce in the form of light at a wavelength substantially different from the wavelength of the light source. The light coming out of the sample to be tested can then be captured by a detector or sensor, which may be selected from, but not limited to, a camera, a charge coupled device (CCD), a complementary metal-oxide-semiconductor (CMOS) (alternatively referred to as a complementary-symmetry metal-oxide-semiconductor (COS-MOS)), one or more individual photodiodes, photodiode arrays (PDAs), avalanche photodiodes (APDs), avalanche photodiodes arrays, PMTs, or PMT arrays.

Known optical or electronic means may be optionally used to amplify the light from the light source and/or the light from the sample to be tested, and/or to separate one or both into its component wavelengths. Selecting a reference spectroscopic substance and one or more sample spectroscopic substances for a particular sample to be tested such that each spectroscopic substance scatters light, selectively absorbs light, emits light in the form of chemiluminescence or fluorescence, depending upon the spectroscopic substance and particular application, at substantially different wavelengths allows for easier separation of the respective wavelengths. The difference between the reference spectroscopic substance's expected value and measured value can be used to quantify the contribution of "noise" to the output, assuming that the reference spectroscopic substance and the one or more sample spectroscopic substances are subject to the same measurement conditions (e.g., the power of the light source, detector or sensor noise, humidity, heat, pH of the sample to be tested, and the vehicle that the sample to be tested itself is in). The contribution of "noise" to the reference spectroscopic substance signal may be designed to at least substantially correlate with the contribution of noise to the signal of the one or more sample spectroscopic substances. This correlation may be, and is typically, proportional but may vary linearly, exponentially, or in other manners or functions.

B. Method

Figure 2:
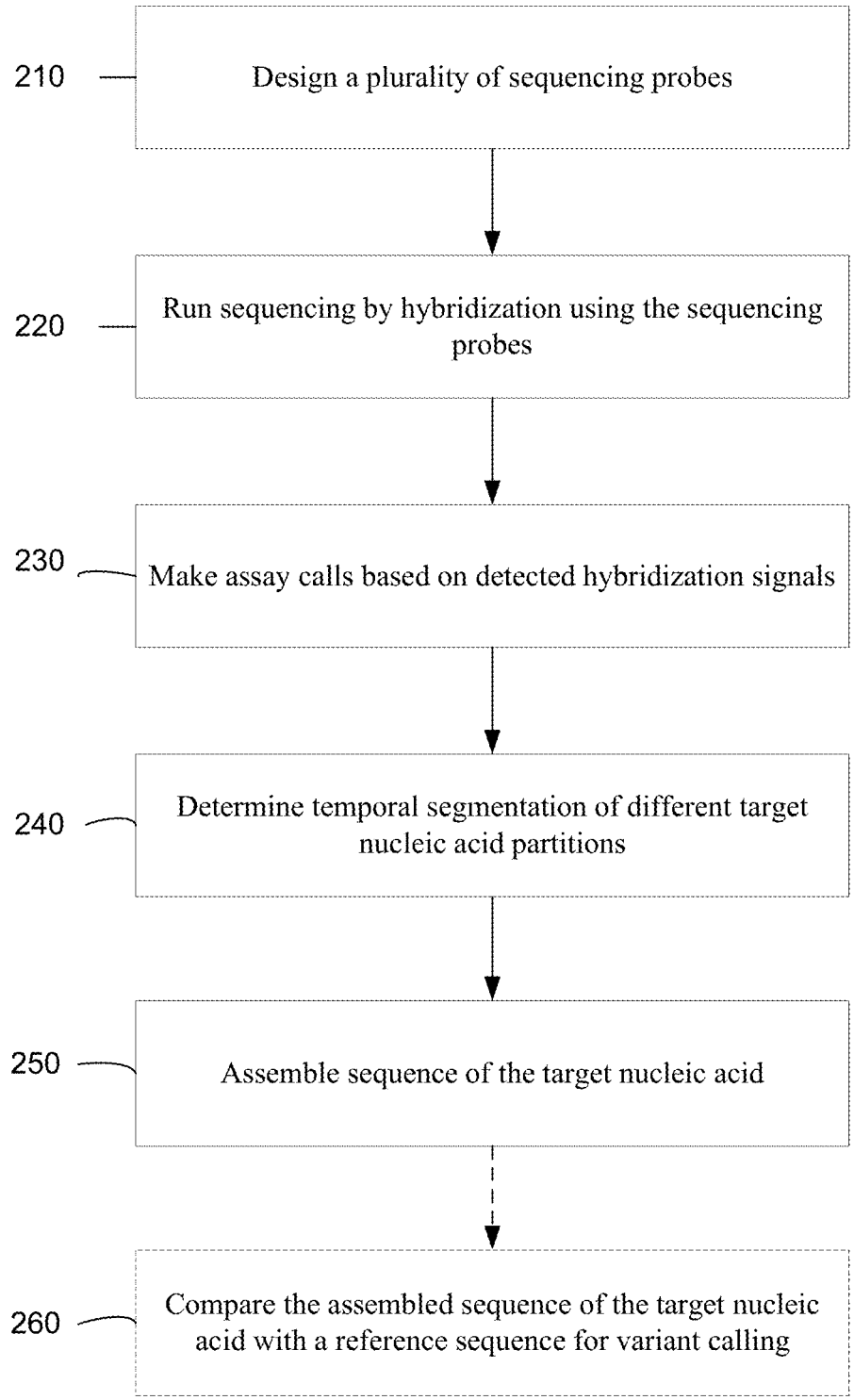
FIG. 2 is a flow chart illustrating a method of genomic sequencing by hybridization according to embodiments of the present invention.

FIG. 2 illustrates a flow chart 200 of a method of sequencing by hybridization, using, for example, microfluidic system 100 of FIG. 1, according to embodiments of the present disclosure.

1. Prior to Sequencing Run

At block 210, prior to sequencing run, a sequencing probe set including a plurality of sequencing probes, for example, oligomers such as hexamers, may be designed as described above. The sequencing probes may include one or more spectroscopic substances that can uniquely identify each sequencing probe. For example, the sequencing probes may each include one or more different dyes at one of several possible concentrations, such as four different dyes each at one of eight possible concentrations, which gives a total of 4096 different combinations, one assigned to each sequencing probe.

FIG. 3A illustrates examples of designed sequencing probes with different dyes and different intensities of each dye assigned to each sequencing probe, represented in a three-dimensional dye space. Each dimension (axis) corresponds to a particular dye color, with the value along a dimension corresponding to an intensity. As shown in the figures, ideally, hybridization signals detected by a detector for each sequencing probe, when mapped to data points in a dye-space, would cluster around a centroid, and the centroids of clusters for all sequencing probes would align to a grid, where the cluster for each sequencing probe is separated from and can be easily distinguished from clusters for other sequencing probes. It is possible that the distribution of data points in each cluster may vary at different regions of the dye space. For example, when an intensity of a dye is high, the absolute value of the variation of the detected signal may be large compared with a dye with a low intensity level, even if the variation may be similar in percentage relative to the intensity level.

Accordingly, each probe would ideally correspond to a different level of intensity for the three color dimensions, and thus correspond to a different multi-dimension data point. But, actual experiments are not ideal, and problems can arise in overlap of clusters and other noise. As discussed in detail below, embodiments can address such problems.

2. Sequencing Run

At block 220 of FIG. 2, the target nucleic acid, the designed sequencing probes, and other reagents may be loaded into a microfluidic system, such as microfluidic system 100 of FIG. 1. Microfluidic system 100 may run the assay as described above, where the hybridization signal of each droplet may be detected while the droplets flow through detector 114. As shown in FIG. 3B, the detected hybridization signals may be continuous in time, and may have different amplitudes corresponding to different dye intensity levels.

3. Assay Calling

At block 230, the detected hybridization signals are processed and assay calling is made for each detected hybridization signal, where each detected hybridization signal corresponds to a reaction droplet. The assay calling can be made by mapping the detected hybridization signals to data points in the dye space as shown in FIG. 3C and comparing with the designed grid as shown in FIG. 3A to determine which sequencing probe is present in each droplet. For instance, the level of intensity of the various dyes (e.g., each detected at a different wavelength) can be used to determine the identity of the sequencing probe, and thus the sequence of every sequencing probe in the reaction droplets. If no error or noise is present, the detected hybridization signal of a reaction droplet would be mapped to a coordinate in the dye space that falls into the cluster for the sequencing probe in each reaction droplet.

FIG. 3C is a scatter plot showing the assay intensity data from a sequencing experiment. Each point in the plot represents the assay fluorescence intensity for a droplet hybridized with a sequencing probe read by the optical detector. Each point is colored according to the fluorescence intensity observed for the droplet containing a target nucleic acid partition and a probe. For example, four different dyes each having eight different concentrations may be used, which provides $8^4$ (or 4096) different combinations in a four dimensional dye space. The points in the scatter plot naturally cluster, wherein each cluster in the figure is a collection of dye intensity readings from droplets that correspond to the same probe, and is colored by the fluorescence identity of the probe. Based on the dye and its intensity assigned to each probe, the sequencing probe hybridized to each droplet may be identified from the fluorescence intensity reading.

Figure 4:
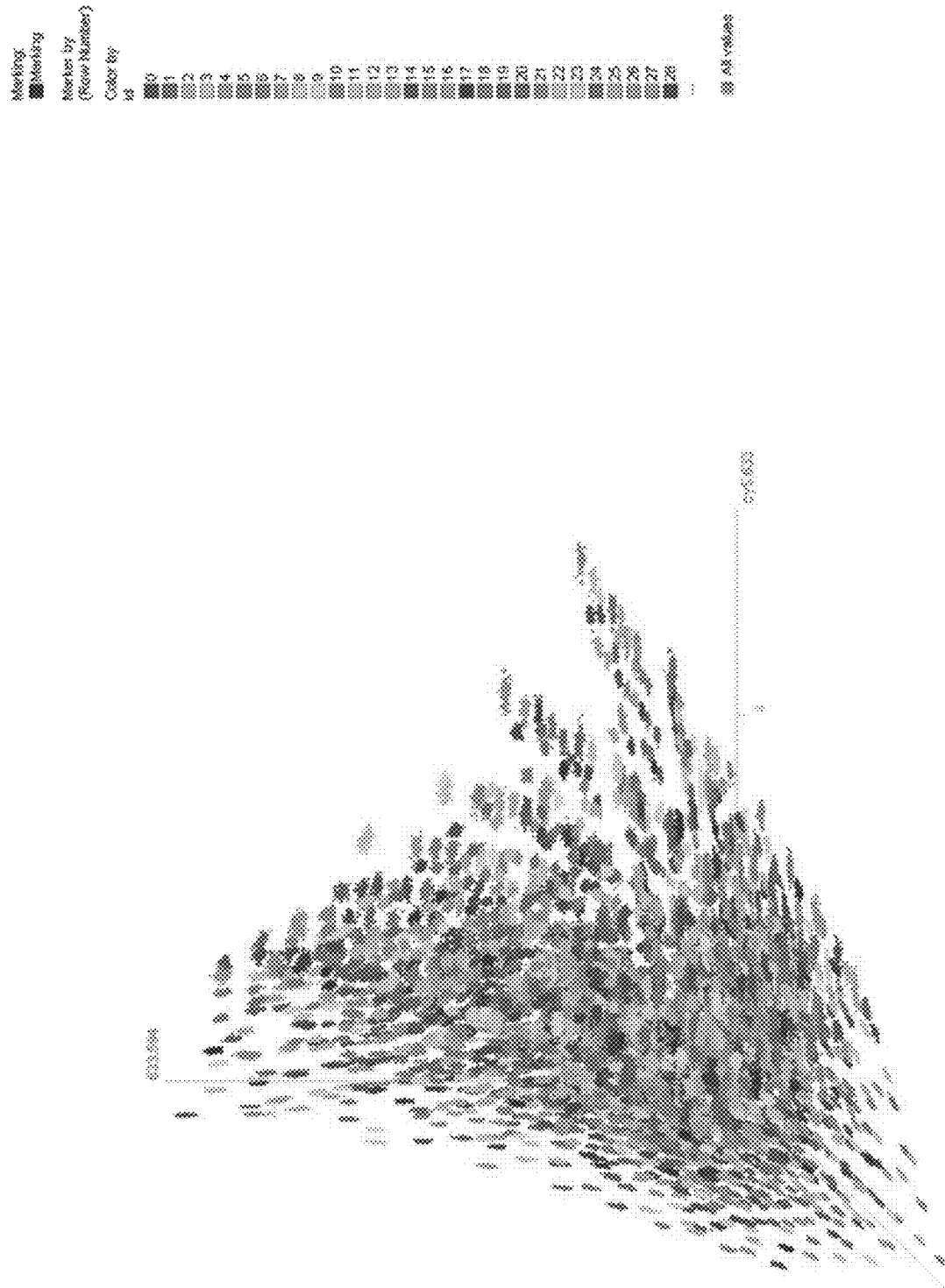
FIG. 4 is a scatter plot illustrating intensity data of hybridization signals from a sequencing by hybridization experiment in a dye space.

FIG. 4 illustrates data points of detected hybridization signals mapped to a multi-dimensional space. As shown in FIG. 4, due to imperfections in the assaying, such as dye dispense variability, drop size variability, pico-injection variability, optical variability and instability, limited headroom in dye space, algorithm limitations, or lack of serial inflation, the data points in the dye space may not cluster around the ideal four dimensional grid of 4096 centroids, and thus the dye space may be densely packed and the clusters may overlap without a clear separation. The data points in FIG. 4 may include many irregularities from an ideal or designed grid as shown in FIG. 3A. Thus, it may be difficult to correctly identify the sequencing probe associated with each data point.

Figure 5C:
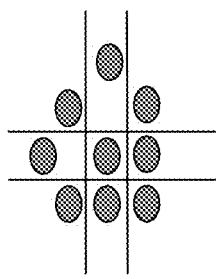
FIG. 5C illustrates some clusters with centroids off from a designed grid in a dye space.
Figure 5F:
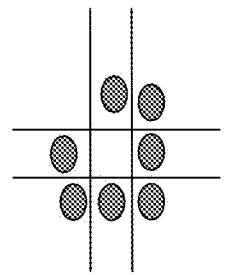
FIG. 5F illustrates that some clusters are missing from designed grid in a dye space.
Figure 5B:
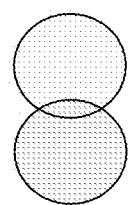
FIG. 5B illustrates two juxtaposed clusters with an overlapping area in a dye space.
Figure 5E:
FIG. 5E illustrates clusters with odd shapes in a dye space.
Figure 5A:
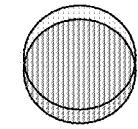
FIG. 5A illustrates two substantially merged clusters in a dye space.
Figure 5D:
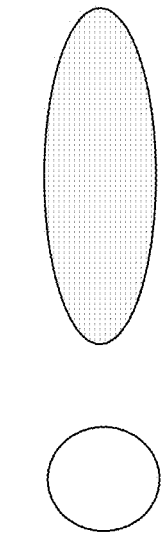
FIG. 5D illustrates different numbers of data points in a unit area for different clusters in a dye space.

FIGS. 5A-5F illustrate some possible irregularities of clusters of detected hybridization signals mapped into a dye space. For example, in FIG. 5A, two clusters are substantially merged. In FIG. 5B, two clusters are juxtaposed with an overlapping area. In FIG. 5C, centroids of some clusters are off from the designed or desired grid. FIG. 5D shows that the number of data points in the unit area may be different for different clusters. In another word, different clusters may have different densities. FIG. 5E shows that some clusters may have odd shapes. FIG. 5F shows that some clusters may be missing from the designed grid.

Various techniques have been employed to solve this problem, such as using quantum dots (Q-dots) or various fluidic geometries. However, these techniques each only deal with one or several, but not all, issues or aspects of the imperfections of the system described above, and do not provide an accurate method for assay calling.

4. Temporal Segmentation of Different Partitions

In a sequencing run, hybridization signals from the reaction droplets may be monitored continuously. Thus, the detected hybridization signals may include hybridization signals of droplets from different target nucleic acid partitions.

At block 240, the edges of signal originating from different target nucleic acid partitions, i.e., when portions from a first target nucleic acid partition are exhausted and partitions from a second target nucleic acid partition (mixed with primer partitions) start, may be detected. Temporal segmentation of different partitions is particularly useful in situations where multiple target nucleic acids are being assayed in the system (e.g., in embodiments in which different primer pairs are used to generate different target nucleic acid partitions, or in the case of allelic variance or sample variation) at least in part because one can subsequently predict and sort the signals from the partitions based on the predicted identity of the target nucleic acid in the partitions.

As an example, if two targets may be present in the system, and the wild-type sequence of each target is known, then one can predict which sequencing probes will hybridize and which will not hybridize to a wild-type reference sequence. This expected pattern of sequencing probe hybridization can then be compared with the actual pattern of primer partition hybridization to determine which target is being assayed in a particular target nucleic acid partition ("slug"). This information can be helpful later when assembling sequences as one will know which hybridization signals applied to one target compared to another target, for example, prior to assembly of the target sequence.

FIG. 3D is a plot showing edges of target nucleic acid partitions according to embodiments of the present invention. The horizontal axis corresponds to partition number, which corresponds to a particular time. The vertical axis corresponds to a contradiction value. A contradiction rate 310 is shown between partition zero and partition 50,000. The contradiction rate is calculated using a sliding window over the partitions. In various embodiments, the center or start of each sliding window can provide the data point at that partition. For example, the contradiction value at partition 10,000 can be determined from the next 2,000 partitions after (possibly including) partition 10,000.

When all partitions correspond to a same mixture drop, the amount of contradictions should be in a minimum level, given that the hybridization status is measuring hybridization to the same target nucleic acid. Whereas, when the partitions are from different mixture drops, the different partitions have hybridization status that are measured against different target nucleic acids; and thus the contradiction rate is at a maximum level. In FIG. 3D, edges 320 between mixture drops (slugs) are shown at the minima of contradiction rate 310 between the peaks. In other embodiments, the edges can be identified at maximum, depending on how the sliding window is defined.

Contradiction rate 310 can be determined as a ratio or a raw number. For the ratio, the numerator can correspond to an amount of partitions that show contradictory hybridization status. The amount can be counted as a number of partitions or a number of primers that show contradictory data. For example, two partitions can have a same primer but have different hybridization status, which can be seen as contradictory data. In various embodiments, the number of partitions that are contradicted can be counted, or the number of primers that are contradicted can be counted.

5. Mapping and Sequence Assembly

At block 250, the resultant information of sequencing probe hybridization can be used in combination with knowledge of the general structure of the target nucleic acid to assemble the sequence of the target nucleic acid based on the presence or absence of hybridization of the sequencing probes as shown in FIG. 3E (genomic DNA=SEQ ID NO:1). In some embodiments, the knowledge of which sequencing probes do not hybridize can also be used in the assembly process. For example, the sequencing probes that do not hybridize can be used to resolve ambiguities of where the sequencing probes that do hybridize can align. Thus, a sequencing probe that hybridizes can be determined not to align to a particular position in the nucleotide sequence, on the basis that a sequencing probe that does not hybridize would align to the resulting sequence if a sequencing probe that does hybridize was placed at the particular position. More detailed techniques of sequence assembly can be found in U.S. patent application Ser. No. 14/290,867, which is incorporated herein by reference for all purposes.

At block 260, the assembled sequence of the target nucleic acid can be compared with a reference or wild-type sequence to determine a variant in the sequence of the target nucleic acid of sample being tested. The identification of the variant can provide various useful information. For example, a diagnosis of a genetic disease may be made.

II. Dye Space Multiplexing Overview

Embodiments of the present application disclose a method for determining a sequence of a target nucleic acid. Embodiments can address situations with high density in dye space, and can improve accuracy in such situations. Embodiments can use a plurality of control oligonucleotides with known sequences and unique identifications (IDs) to map hybridization signals associated with a plurality of sequencing probes to a loosely packed multi-dimensional dye space, such that a region in the dye space is associated with one or more sequencing probes. When a detected target hybridization signal of a sequencing probe and a target nucleic acid is mapped to the multi-dimensional dye space, the sequencing probe and thus the corresponding nucleotides in the target nucleic acid can be determined based on the sequencing probe(s) associated with the region that the detected target hybridization signal is mapped to.

Figure 6:
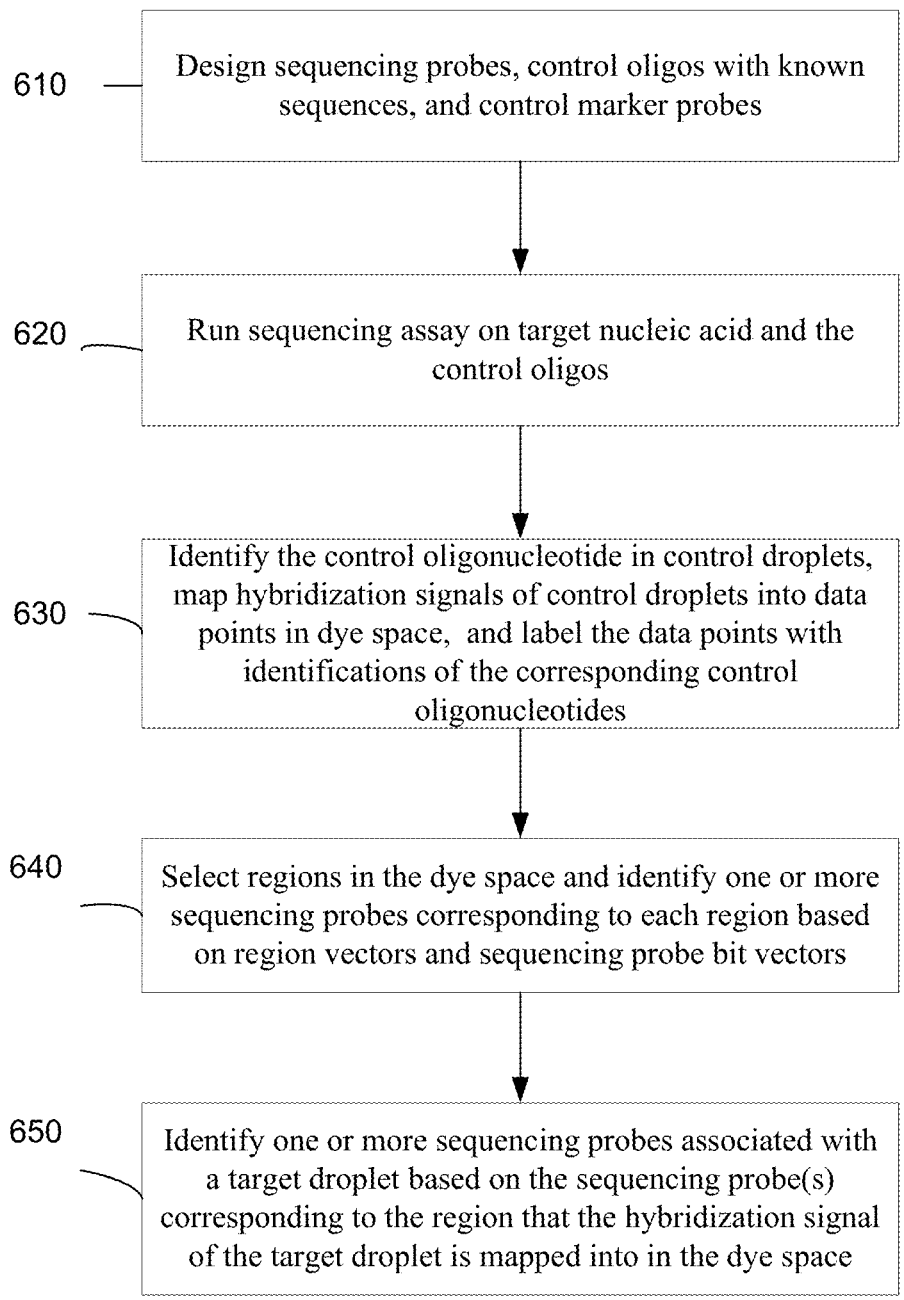
FIG. 6 is a flow chart illustrating a method for determining a sequence of a target nucleic acid according to embodiments of the present invention.

FIG. 6 illustrates a flow chart 600 of a method for determining a sequence of a target nucleic acid according to embodiments of the present disclosure. The method can be performed using physical steps and steps performed on a computer.

At block 610, before sequencing, a plurality of sequencing probes, such as hexamers, are designed. A plurality of control oligonucleotides can also be designed, each with a known sequence of about a few hundreds of nucleotides. Each control oligonucleotide has a unique identification (ID) associated with it. The unique ID may be a unique control marker that can hybridize with one or more of a plurality of control marker probes. The plurality of control oligonucleotides may include nucleotide sequences that can hybridize with any sequencing probe such that any sequencing probe may be mapped to the loosely packed dye space using the control oligonucleotides. Based on the known sequences of the control oligonucleotides, a sequencing probe bit vector can be determined for each sequencing probe identifying the control oligonucleotides that can hybridize with the sequencing probe.

At block 620, during each sequencing run, the control oligonucleotides can be sequenced with the target nucleic acid or target partitions of the target nucleic acid in a same sequencing run, using the plurality of sequencing probes and the plurality of control marker probes in a system as described above. For example, each partition of control oligonucleotide or each partition of the target nucleic acid may be split into a plurality of droplets, and each droplet can be mixed with a sequencing probe or a control marker probe. In this way, system variations, errors or other imperfections during the sequencing run will have similar effects on the sequencing of the control oligonucleotides and the target nucleic acids, and thus can be calibrated out based on the known sequences of the control oligonucleotides.

In each sequencing run, control hybridization signals of control oligonucleotides hybridized with sequencing probes, target hybridization signals of target nucleic acids hybridized with sequencing probes, and control marker hybridization signals of control oligonucleotides hybridized with control marker probes can be detected.

At block 630, control hybridization signals of control oligonucleotides hybridized with sequencing probes can be identified and labeled with the IDs of the corresponding control oligonucleotides using, for example, control marker probes that can hybridize with control markers in the control oligonucleotides, based on a temporal stream of detected control hybridization signals. The detected control hybridization signals can be mapped to multi-dimensional control data points in a dye space, and stored with the corresponding identified IDs. The multi-dimensional control data points labeled with IDs may cluster in the dye space.

At block 640, based on the clustered multi-dimensional control data points labeled with IDs, a region vector may be created for any region in the dye space. The region vector can identify the control oligonucleotides that correspond to the multi-dimensional control data points mapped to the region based on the stored IDs associated with each control data points. The region vector can be compared against each sequencing probe bit vector to determine one or more sequencing probes corresponding to the region. The size of the region may be selected to find a best match between the region vector of the region and a sequencing probe bit vector.

At block 650, after the sequencing run or during the sequencing run, target hybridization signals of target droplets, including copies of the target nucleic acids, may also be mapped to multi-dimensional target data points in the dye space. For each target data point in the dye space, one or more sequencing probes may be associated with the target data point based on the one or more sequencing probes corresponding to the region that the target data point falls into in the dye space.

Alternatively, when a target hybridization signal is detected and mapped to a multi-dimensional target data point in the dye space, a region including the mapped target data point may be selected and a region vector may be created for the region. The region vector may be compared with each sequencing probe bit vector to determine the sequencing probe(s) corresponding to the region in the dye space.

In this way, the target nucleic acid can be sequenced by the plurality of sequencing probes, and the sequencing probes that hybridize with the target nucleic acid may be identified. Based on the sequencing probes that hybridize with the target nucleic acid, an assembly process may be performed to determine the sequence of the target nucleic acid using, for example, methods described in U.S. patent application Ser. No. 14/290,867.

Further details of the method described in flow chart 600 of FIG. 6 are provided below.

III. Designing Control Oligonucleotides with Control Marker

Figure 7:
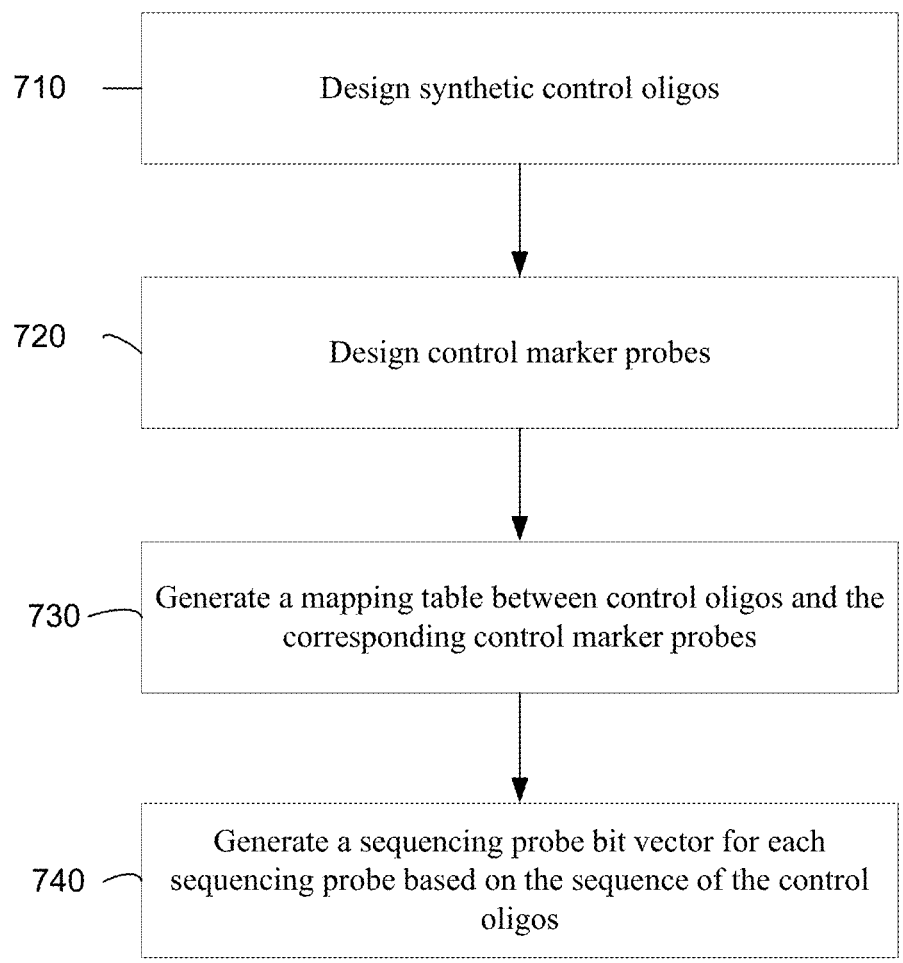
FIG. 7 is a flow chart illustrating a method of designing control oligonucleotides.

FIG. 7 illustrates an embodiment of a flow 700 for designing control oligonucleotides. Flow 700 may be performed for block 610.

At block 710, a plurality of control oligonucleotides may be designed and synthesized based on the plurality of sequencing probes used for target nucleic acid sequencing. For example, the sequencing probes may be N-base probes, such as hexamers that include six nucleotides, and the plurality of sequencing probe may include $4^N$ different N-base probes. For example, the plurality of sequencing probe may include $4^6$ or 4096 different hexamers. In some embodiments, less than $4^N$ different N-based probes may be used. The plurality of control oligonucleotides may be designed to include a certain number of control oligonucleotides that include sequences that can hybridize with each sequencing probe. For example, when 4096 different hexamers are used as sequencing probes, about 400 different control oligonucleotides each including about 200 base pairs, or about 800 different control oligonucleotides, each including about 100 base pairs, may be designed such that each sequencing probe may be able to hybridize with about 5 to about 35 different control oligonucleotides, or an average of about 20 different control oligonucleotides. It is noted that the above numbers are for illustration purposes only. Other lengths and numbers of control oligonucleotides, and the number of different control oligonucleotides that can hybridize with each sequencing probe may be used as appropriate.

In some embodiments, the plurality of control oligonucleotides may be synthesized oligonucleotides. In some embodiments, the plurality of control oligonucleotides may be plasmids with known sequence.

At block 720, depending on the number of control oligonucleotides used, control markers attached to the control oligonucleotides and the corresponding control marker probes may be designed to uniquely identify each control oligonucleotide. The control marker probes may be different from sequencing probes in, for example, number of base pairs, such that the hybridization signals of the control marker probes hybridized with control oligonucleotides may be mapped to multi-dimensional data points in the dye space in protected regions separated from the data points mapped for the detected control hybridization signals and target control hybridization signals associated with sequencing probes.

Figure 8:
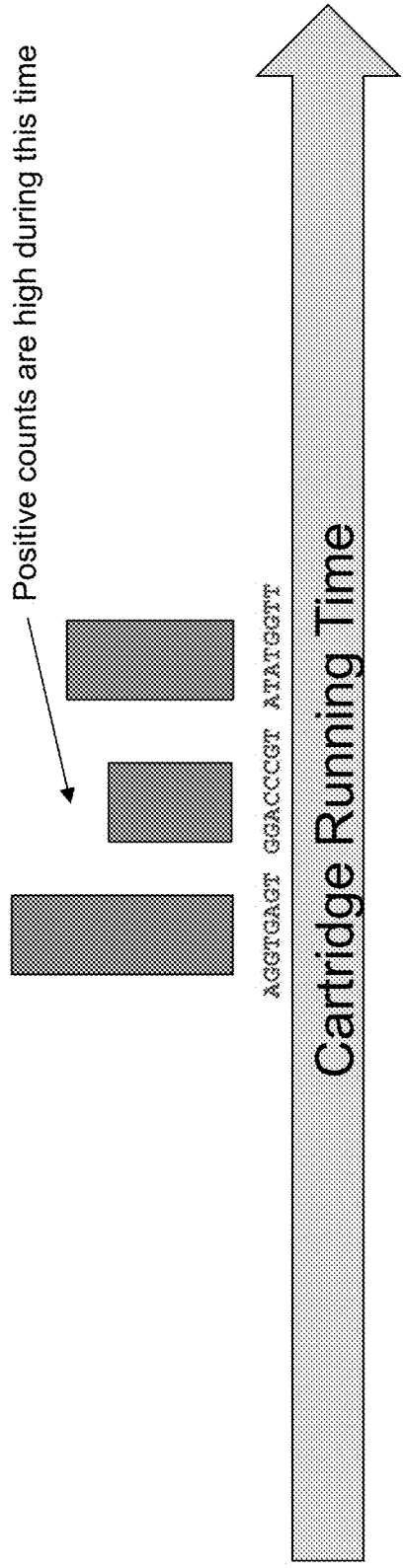
FIG. 8 illustrates an example of control marker probe design (24mer=SEQ ID NO:2).

FIG. 8 illustrates an example of control marker probe design. In the example shown in FIG. 8, about 400 control oligonucleotides each including about 200 base pairs, and about 15 unique control marker probes are used. Each control marker probe includes 8 bases. Three control marker probes may be chosen for each control oligonucleotide, and a 24-base control marker that can hybridize with the three control marker probes may be attached to each control oligonucleotide. For example, AGGTGAGT, GGACCCGT, and ATATGGTT (24mer=SEQ ID NO:2) may be used to label one control oligonucleotide. Thus, each control oligonucleotide may actually include about 224 base pairs. Because there can be about $15 \times 14 \times 13/(3 \times 2)=455$ different combinations of three control marker probes chosen from 15 control marker probes, the about 400 control oligonucleotides can be uniquely identified by the different combinations of three control marker probes chosen from 15 control marker probes as control oligonucleotide 1, control oligonucleotide 2, . . . and control oligonucleotide 400. In this way, each control oligonucleotide may be assigned a unique identification (ID) that can be detected using the control marker probes. If more control oligonucleotides are used, more control marker probes, such as 4, 5 or more control marker probes may be chosen from the 15 control marker probes. Other methods of identifying a control oligonucleotide may be used, such as using radioactive phosphates, biotin, fluorophores, or enzymes.

At block 730, a mapping table between the designed control nucleotides and the control marker probes may be created for use in sequencing experiments to identify the control nucleotides. FIG. 9 illustrates an example table for encoding the control oligonucleotide ID using three different control marker probes. For example, control oligonucleotide 1 may be designed to hybridize with control marker probes 1, 5 and 8; control oligonucleotide 2 may be designed to hybridize with control marker probes 1, 8 and 13; . . . and control oligonucleotide 400 may be designed to hybridize with control marker probes 11, 14 and 15. Thus, for the example shown in FIG. 8, if control marker hybridization signals associated with control marker probes number 1 (AGGTGAGT), number 8 (GGACCCGT), and number 13 (ATATGGTT) can be detected more frequently within a time period during the sequencing, it may be determined that the droplets detected within the time period are reaction droplets injected with portions of a partition or slug including control oligonucleotide 2.

At block 740, a sequencing probe bit vector may be created for each sequencing probe based on the known sequence of each design control oligonucleotide. Each bit in a sequencing probe bit vector indicates whether the sequencing probe can hybridize with the corresponding control oligonucleotide.

FIG. 10 illustrates examples of sequencing probe bit vectors for 4096 hexamer sequencing probes using 400 control oligonucleotides, each including about 200 base pairs. In FIG. 10, each sequencing probe bit vector 1010 includes 400 bits, where each bit 1020 corresponds to one of the 400 control oligonucleotide. A "1" in a bit in a sequencing probe bit vector indicates that the corresponding control oligonucleotide can hybridize with the sequencing probe, and a "0" in a bit indicates that the corresponding control oligonucleotide cannot hybridize with the sequencing probe. For example, in the example shown in FIG. 10, the sequencing probe bit vector for sequencing probe AGTCAG shows that sequencing probe AGTCAG can hybridize with control oligonucleotides 1, 5, 6, 9, 10, . . . and 400, but cannot hybridize with control oligonucleotides 2-4, 7, 8 . . . . A sequencing probe bit vector may be generated for each sequencing probe used in the sequencing. As described above, in some embodiments, each sequencing probe bit vector may have about 5 to about 35 "1s," or an average of about 20 "1s." Furthermore, because each control oligonucleotide may include 200 base pairs, each control oligonucleotide may be able to hybridize with up to about 200 different sequencing probes.

IV. Sequencing Assay

When a target nucleic acid needs to be sequenced, a microfluidic device, such as microfluidic system 100 of FIG. 1, may be used for serialized pipelined sequencing by hybridization (SBH).

Figure 11:
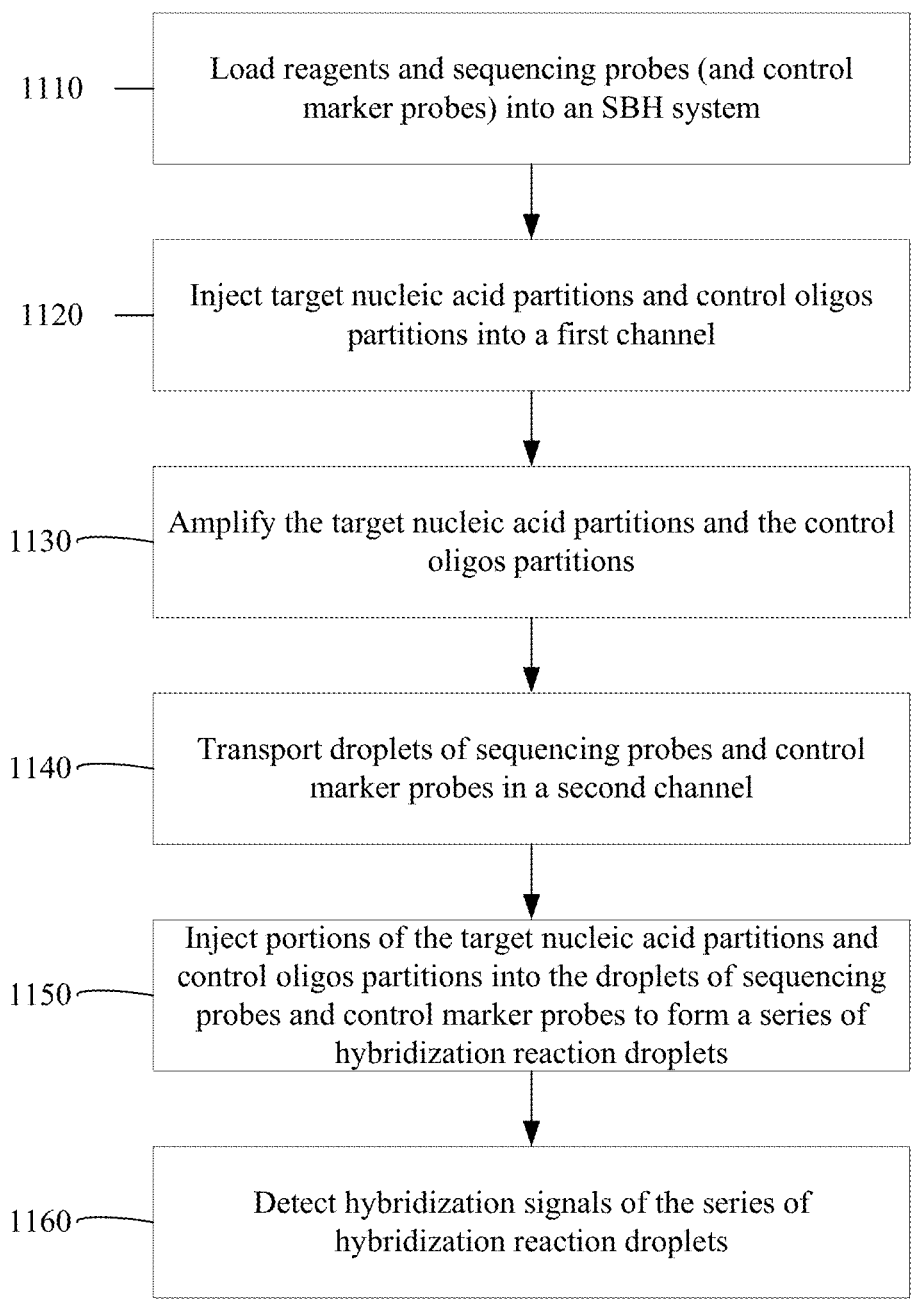
FIG. 11 is a flow chart illustrating a process of sequencing by hybridization.

FIG. 11 is a flow chart illustrating a flow 1100 of sequencing by hybridization using a microfluidic SBH system, such as microfluidic system 100 of FIG. 1. Flow 1100 may be performed for block 620.

At block 1110, reagents, sequencing probes, and control marker probes (if used) may be loaded into microfluidic system 100. The two reservoirs of microfluidic system 100 can be loaded with emulsified reagents. Reservoir A may be loaded with emulsified reagents necessary for performing a PCR reaction, including at least one PCR primer pair 102 and other PCR reagents, such as polymerases. Reservoir B may be loaded with emulsified reagents necessary for the sequencing, including the plurality of sequencing probes 104, such as, for example, 4096 different types of hexamers, and control marker probes, such as 15 different octamers as described above. Each of the sequencing probes may include one or more different dyes at one of several possible concentrations, such that the concentration of the different dyes indicates the identity of the sequencing probe. For example, each sequencing probe may include 4 different dyes, each at one of 8 possible concentrations, such that each sequencing probe may be mapped to one of $8^4$ or 4096 different locations in a multi-dimensional dye space. The control marker probes may each include a different number of dyes at one of a different number of possible concentrations compared with the sequencing probes.

At block 1120, target nucleic acid partitions and control oligonucleotide partitions can be injected into a microfluidic channel for amplification. For example, at injection point C of microfluidic system 100, a portion of the target nucleic acid 106 or one control oligonucleotide of the plurality of control oligonucleotides can be injected into each of a plurality of PCR partitions or slugs 108 in microfluidic channel 116. In various embodiments, only a portion of PCR partitions or slugs 108 is injected with control oligonucleotides, wherein each PCR partition or slug 108 injected with control oligonucleotides only includes one type of control oligonucleotide of the plurality of control oligonucleotides. For example, only about 5%, about 10%, or about 20% of PCR partitions or slugs 108 is injected with control oligonucleotides. Other PCR partitions or slugs 108 are injected with target nucleic acid 106. As an example, a total of about 4000 PCR partitions or slugs 108 may be injected with target nucleic acid 106 or control oligonucleotides, among which, about 400 partitions or about 10% may be injected with control oligonucleotides, each being injected with only one type of control oligonucleotide.

At block 1130, the target nucleic acid partitions and control oligonucleotides partitions may be amplified at, for example, serpentine channel 112 in section D of microfluidic system 100. The serpentine channel in section D may include at least two distinct thermal zones and acts as an online thermal cycler. Each of the PCR partitions or slugs 108 flows through the serpentine channel and is amplified in the channel. The amplification reaction may also introduce a fluorescent molecule to an end of a target partition of the target nucleotide acid.

At block 1140, droplets of sequencing probes and control marker probes are transported from, for example, reservoir B, along a second channel, such as microfluidic channel 118. Each droplet may include one sequencing probe or one control marker probe. In some embodiments, each droplet may include more than one sequencing probe or one control marker probe. A small portion of the droplets in microfluidic channel 118, such as less than about 5%, about 10%, about 15%, or about 20%, may be droplets including control marker probes.

At block 1150, when each amplified PCR partition or slug 108 including a target nucleic acid partition or control oligonucleotide partitions reaches the second injection point E, portions of the amplified PCR partition or slug 108 may be injected into the droplets comprising different sequencing probes or control marker probes traveling in microfluidic channel 118 to form a series of reaction droplets 110, such as 4000 or more reaction droplets each including a different sequencing probe or control marker probe. In each reaction droplet, the sequencing probe or the control marker probe may hybridize with the target nucleic acid or the control oligonucleotide if the sequencing probe or the control marker probe matches a piece of the target partition of the target nucleic acid or the control oligonucleotide. In some embodiments, about 5%, about 10%, about 20% or less of the reaction droplets includes control marker probes.

At block 1160, the reaction droplets flow downstream of injection point E and are detected by detector 114, such as an optical detector, at point F. Detector 114 at point F may detect a fluorescent signal as a hybridization signal from each reaction droplet, as described above. The detected hybridization signal may include intensities of different dyes for a positive hybridization. The detected hybridization signal may also indicate that there is no hybridization or a negative hybridization in a reaction droplet. For clarity, detected hybridization signals from reaction droplets including the target nucleic acid are referred to as target hybridization signals, while detected hybridization signals from reaction droplets including a control oligonucleotide are referred to as control hybridization signals.

Figure 12:
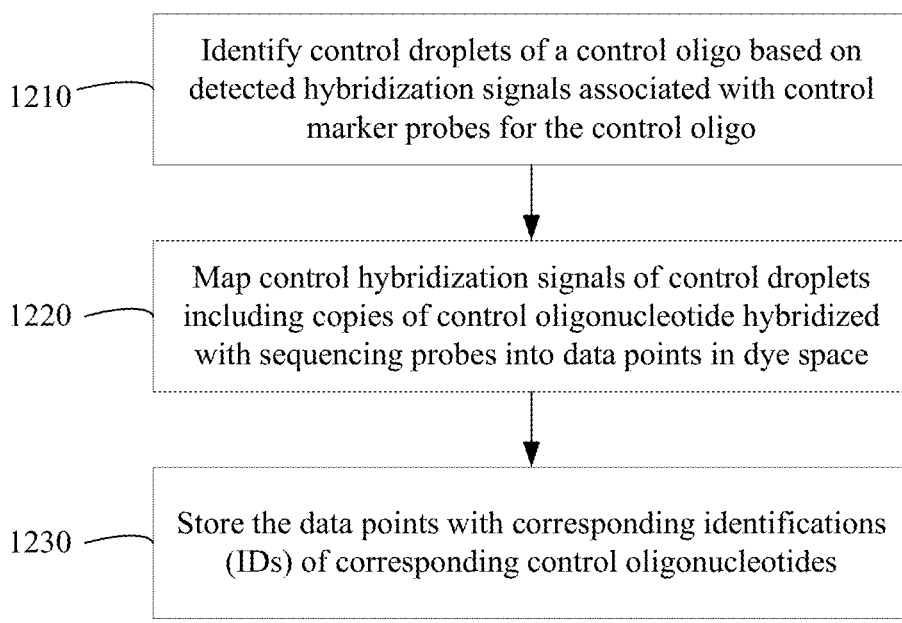
FIG. 12 is a flow chart illustrating a process of identifying control oligonucleotides and mapping detected hybridization signals of control oligonucleotides to control data points in a dye space.

V. Identifying Control Oligonucleotides and Mapping Control Hybridization Signals FIG. 12 is a flow chart illustrating a flow 1200 of identifying control oligonucleotides and mapping detected control hybridization signals of control oligonucleotides to data points in a dye space. Flow 1200 may be performed for block 630.

At block 1210, control hybridization signals of control oligonucleotides hybridized with sequencing probes can be identified. The control hybridization signals can be labeled with the IDs of the corresponding control oligonucleotides, using, for example, control marker probes that can hybridize with control markers in the control oligonucleotides as described above, based on a temporal stream of detected control hybridization signals.

In the sequencing run, the detected hybridization signals may include hybridization signals of target nucleic acid or control oligonucleotide hybridized with sequencing probes or control marker probes. In some embodiments, detected control hybridization signals of control oligonucleotides hybridized with control marker probes in a temporal stream may be used to separate control hybridization signals from target hybridization signals, and identify the control oligonucleotide with its assigned control marker and ID.

For example, as discussed above, a partition or slug 108 in the sequencing run may include one type of control oligonucleotide that includes a unique 24-base control marker, and may be injected into a series of droplets comprising different sequencing probes or control marker probes to form a series of reaction droplets. Thus, during a time window in the temporal stream of detected hybridization signals, hybridization signals associated with three octamer control marker probes may appear frequently. The frequent appearance of hybridization signals associated with three control marker probes indicates that, during the time window, reaction droplets injected from a partition or slug 108 having a control oligonucleotide that includes a control marker matching the three control marker probes were being detected by the detector. As described above, hybridization signals associated with control marker probes may be mapped to the protected region in a dye space and may be relatively easy to detect and identify.

Based on the identities of the three control marker probes and a look-up table, such as the one shown in FIG. 9, the corresponding particular control oligonucleotide may be identified with its assigned ID. Once the time window and the associated particular control oligonucleotide detected during the time window are identified, all or most of the detect hybridization signals within the time window can be identified as control hybridization signals associated with the particular control oligonucleotide, and can be labeled with the ID of the particular control oligonucleotide.

As discussed above, the method of identifying or detecting control oligonucleotides is not limited to using three hexamers control marker probes chosen from, for example, 15 different hexamers control marker probes. Other methods of identifying each control oligonucleotide may be used.

At block 1220, based on the identified control hybridization signals and the associated control oligonucleotide IDs, the detected control hybridization signals that include information of different intensities of different dyes can be mapped to multi-dimensional control data points in a dye space. Similarly, detected target hybridization signals associated with the target nucleic acid may be mapped to multi-dimensional target data points in the same dye space.

Figure 13:
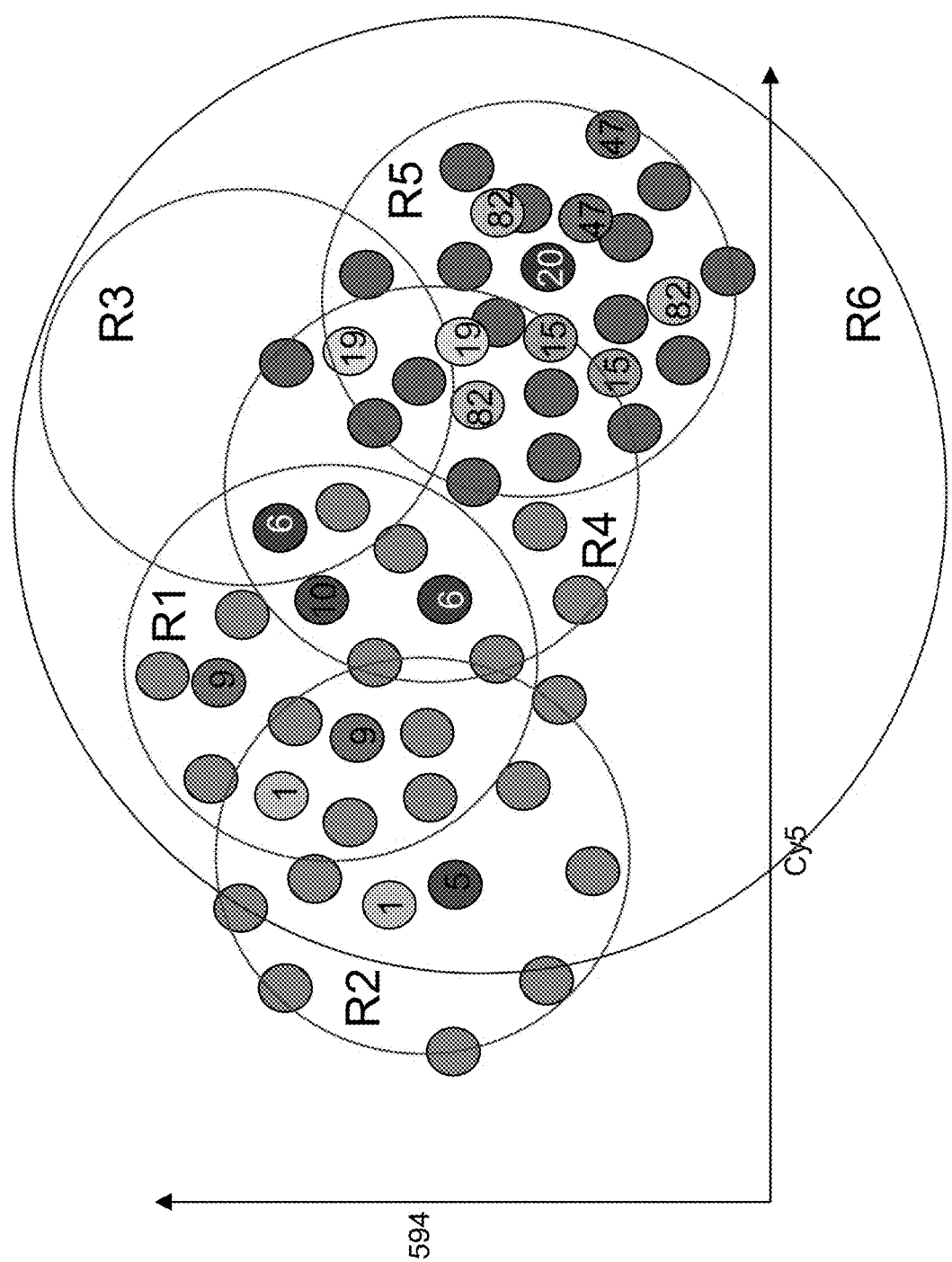
FIG. 13 illustrates detected control hybridization signals mapped to control data points in a dye space and stored with the corresponding control oligonucleotide identifications.

At block 1230, the mapped multi-dimensional control data points in the dye space can be stored with the corresponding identified IDs, as shown in FIG. 13, along with target data points. For ease of illustration, a two-dimensional dye space is shown in FIG. 13. It should be understood that the dye space may be a multi-dimensional space, such as three-dimensional, 4-dimensional, 5-dimensional or more.

In FIG. 13, each filled circle corresponds to a data point mapped from a hybridization signal detected from a reaction droplet, filled circles with a numerical label are data points corresponding to detected control hybridization signal, and filled circles without a numerical label are data points corresponding to detected target hybridization signals. For example, orange circles labeled with "1" in FIG. 13 are data points corresponding to control hybridization signals detected from reaction droplets including control oligonucleotide 1, green circles labeled with "9" are data points corresponding to control hybridization signals detected from reaction droplets including control oligonucleotide 9, and so on. As also shown in FIG. 13, the multi-dimensional control data points labeled with control oligonucleotide IDs may cluster in the dye space. For example, data points associated with control oligonucleotides 1, 5, 9 and 10 cluster in region R1, data points associated with control oligonucleotides 15, 19, 20, 47 and 82 cluster in region R5, and so on.

VI. Identifying Regions and Sequencing Probes Associated with the Regions in Dye Space After the control hybridization signals are mapped to data points in the dye space and labeled with corresponding control oligonucleotide IDs, one or more sequencing probes may be associated with a given region in the dye space with a probability level associated with each of the one or more sequencing probes, based on data points in the region labeled with corresponding control oligonucleotide IDs. A region vector can be created for the region to identify the control oligonucleotides that correspond to the control data points mapped to the region based on the stored IDs associated with each control data points. The region vector can be compared against each sequencing probe bit vector to determine the one or more sequencing probes corresponding to the region. Alternatively, the one or more sequencing probes associated with a region in the dye space may be determined when a target hybridization signal to be identified or called is mapped into a target data point in the region.

Figure 14:
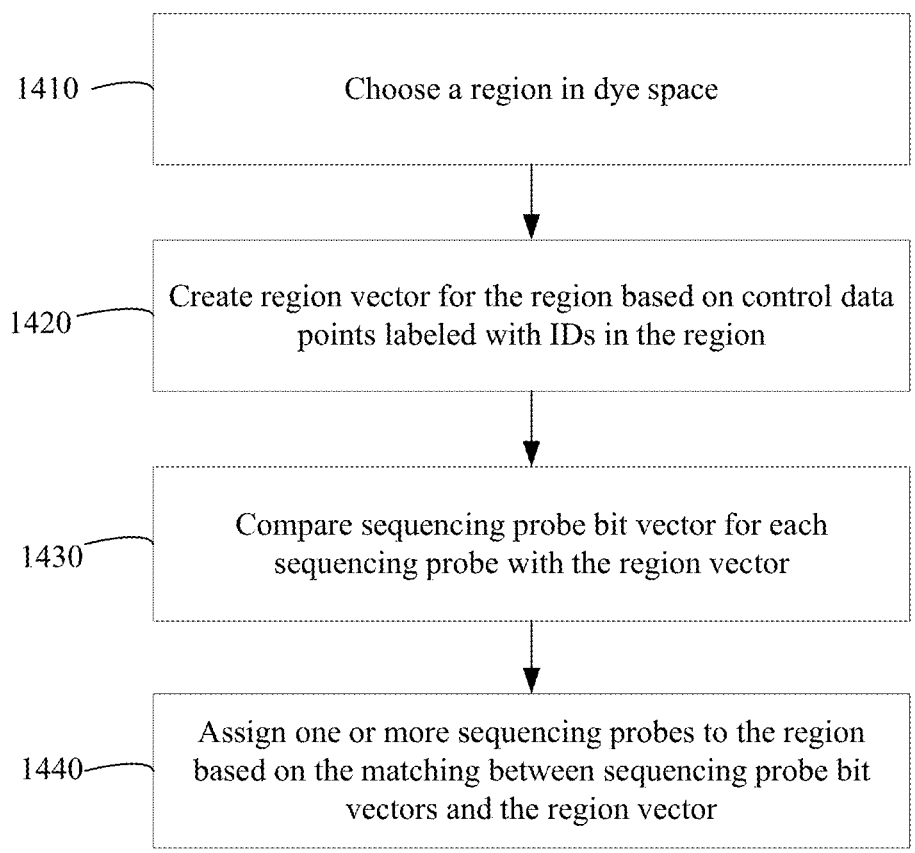
FIG. 14 is a flow chart illustrating a method of identifying regions and sequencing probes associated with the regions in a dye space.

FIG. 14 illustrates a flow 1400 of a method of identifying regions and sequencing probes associated with the regions in dye space. Flow 1400 may be performed for block 640.

At block 1410, a region is selected in the dye space. The region may be any suitable region. For example, in a two-dimensional space, the region may be a circle, a square, an ellipse, a rectangle or other shape of various sizes. The example in FIG. 13 shows circular regions R1-R6 of different sizes.

In some embodiments, a compression ratio can be used to select a region. The compression ratio may be determined by dividing the total number of different control oligonucleotide IDs in the region, that is, the number of bits in a region vector as described below, by the total number of data points in the region that corresponds to control oligonucleotides. The compression ratio may at least partially indicate the coherence of the region, that is, the homogeneity of the identity of the region. In some embodiments, the coherence of the region may be represented by the Shannon entropy of the region. The compression ratio may strongly correlate with the Shannon entropy of the region. When the compression ratio gets closer to zero, the Shannon entropy of the region gets closer to zero as well. Generally, the lower the compression ratio, the lower the Shannon entropy and the more homogeneous the identity of the region.

At block 1420, a region vector may be created for the selected region. The region vector for a region may be of the same size as the sequencing probe bit vector. For example, if 400 control oligonucleotides are used, each region vector may include 400 values. Each value in the region vector corresponds to one control oligonucleotide and represents a contribution of any multi-dimensional control data points that are within the region and have the ID of the corresponding control oligonucleotide.

Figure 15:
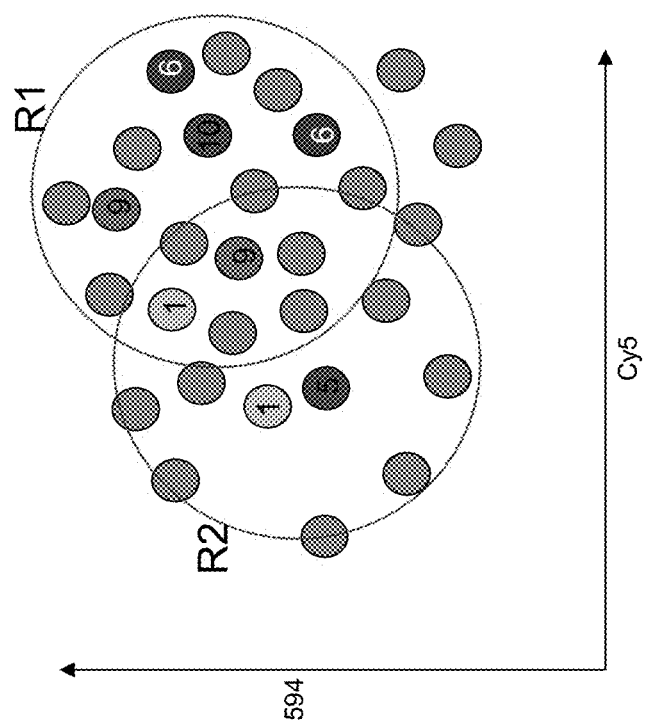
FIG. 15A illustrates examples of regions in a two-dimensional space.
FIG. 15B illustrates examples of region vectors for the regions shown in FIG. 15A.

For example, FIG. 15A illustrates examples of regions in a two-dimensional space, and FIG. 15B illustrates examples of region vectors for the regions shown in FIG. 15A. As shown in FIG. 15A, multi-dimensional control data points in circular region R1 include one data point corresponding to control oligonucleotide 1, two data points corresponding to control oligonucleotide 6, two data points corresponding to control oligonucleotide 9 and one data point corresponding to control oligonucleotide 10. Thus, the region vector for region R1 may be written as (1, 0, 0, 0, 0, 2, 0, 0, 2, 1, . . . ) as shown in FIG. 15B, where each value indicates the number of data points corresponding to each control oligonucleotide that falls in region R1. Similarly, multi-dimensional control data points in circular region R2 include two data points corresponding to control oligonucleotide 1, one data point corresponding to control oligonucleotide 5, and one data point corresponding to control oligonucleotide 9. Thus, the region vector for region R2 may be written as (2, 0, 0, 0, 1, 0, 0, 0, 1, 0, . . . ) as shown in FIG. 15B, where each value indicates the number of data points corresponding to each control oligonucleotide that falls in region R2.

Figure 16:
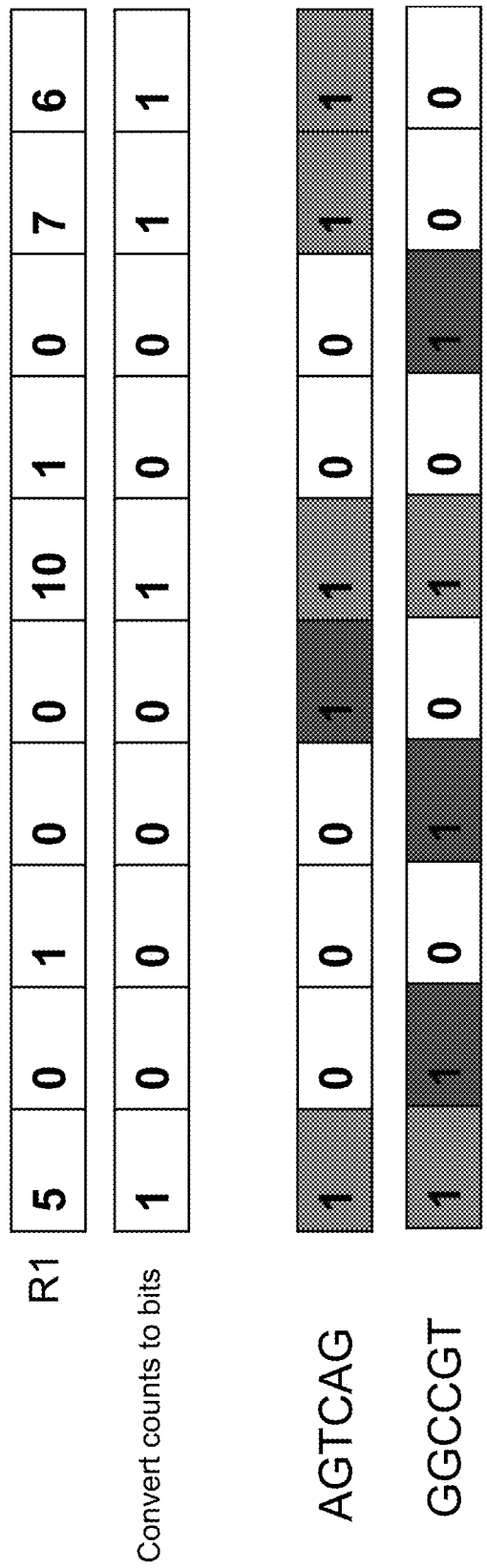
FIG. 16 illustrates region vectors with binary bit values.

In some embodiments as shown in FIG. 16, values in the region vector may be converted into binary bits. For example, any value in the region vectors larger than 0 can be converted to "1." In some embodiments, if a value is less than a threshold value, the value may be converted to "0" as the data points may be mapped to the region due to noise or error or may be associated with the corresponding control oligonucleotide due to error or noise. For example, in FIG. 16, region vector for region R1 shows that one data point associated with control oligonucleotide 3 or 7 falls into region 1. This may be caused by error or noise. Thus, in the converted binary region vector, a "0" is assigned to each of bit 3 and bit 7. For control oligonucleotides 1, 6, 9 and 10, because more than a threshold number (such as 2, 3, or 4) of data points fall in region R1, a "1" is assigned to each of bits 1, 6, 9 and 10. A resultant region vector for R1 may therefore be written as (1, 0, 0, 0, 0, 1, 0, 0, 1, 1, . . . ) as shown in FIG. 16.

At block 1430, the region vector may be compared with each sequencing probe bit vector to find a best match between the region vector and one or more sequencing probe bit vectors. The comparison may be done by, for example, bit-wise exclusive OR (XOR) of the region vector with each sequencing probe bit vector. The sequencing probes may be ranked for a region based on, for example, their corresponding surprisal values. For example, as shown in FIG. 16, for region R1 with a region vector of (1, 0, 0, 0, 0, 1, 0, 0, 1, 1, . . . ), sequencing probe AGTCAG, which has a sequencing probe bit vector of (1, 0, 0, 0, 1, 1, 0, 0, 1, 1, . . . ), may be found to be the sequencing probe with a best matching sequencing probe bit vector to the region vector, because the sequencing probe bit vector for AGTCAG has only 5 bits with a value of 1 out of about 400 bits, yet it has 4 bits that are in common with region vector for region R1, which corresponds to a surprisal value of about $$\ln_2\left(\frac{1}{\frac{5}{400} \times \frac{4}{400}}\right)^4 = 51.86 \text{ bits.}$$

Sequencing probe bit vector for GGCCGT only has two bits in common with region vector for region R1, and thus has a surprisal value of about 25.93 bits.

At block 1440, one or more sequencing probes may be assigned to the region based on the matching between sequencing probe bit vectors and the region vector. For example, in the example shown in FIG. 16, sequencing probe AGTCAG may be associated with region R1 in the dye space. Any reaction droplet with a detected target hybridization signal mapped into a data point in region R1 can be determined to include sequencing probe AGTCAG, and thus the target nucleic acid in the reaction droplet includes a sequence of TCAGTC.

In some embodiments, if it is determined that a smaller region corresponds to a sequencing probe, a larger region that includes the smaller region may be selected and the sequencing probes associated with the area may be determined. If the larger region is also determined to be only associated with the same sequencing probe associated with the smaller region, that is a strong indication that the smaller region is coherent.

In some embodiments, when the surprisal values of the top few sequencing probes for a region are close, for example, when the surprisal value of the top sequencing probe in the ranking is less than 20% more than the surprisal value of the second sequencing probe in the ranking, one or more sequencing probes may be assigned to a region.

Figure 17:
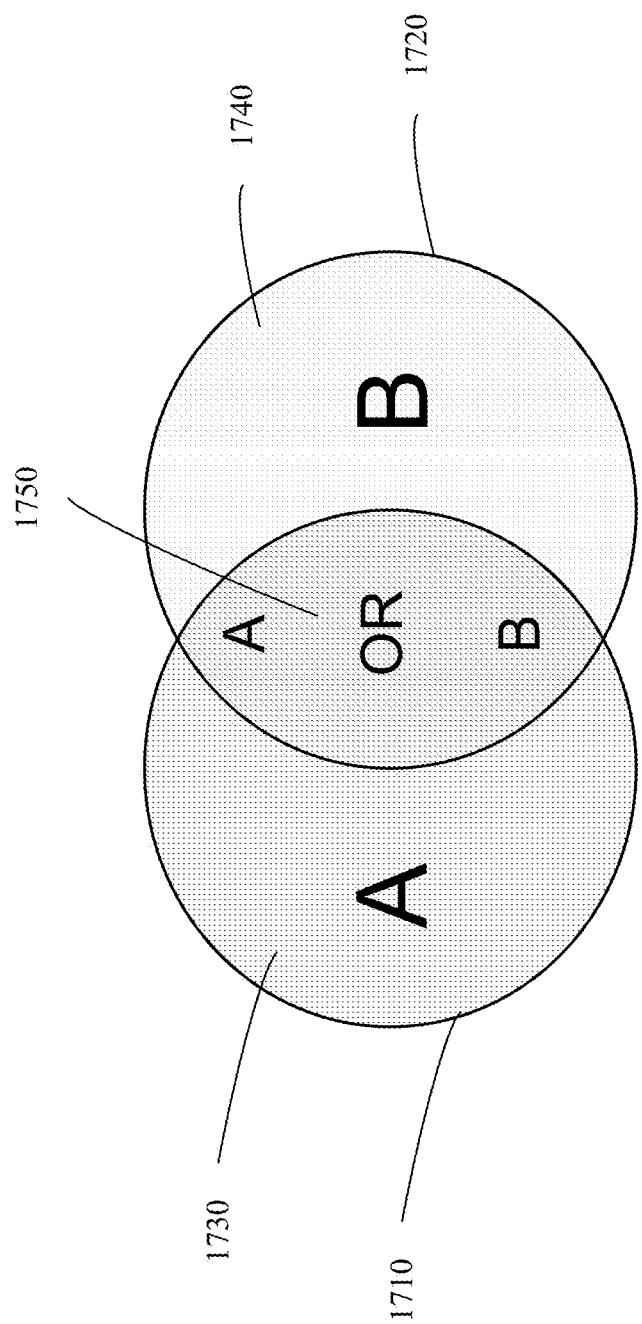
FIG. 17 illustrates a region associated with more than one sequencing probes in a dye space.

FIG. 17 illustrates an embodiment where more than one sequencing probe may be assigned to a region. As shown in FIG. 17, area 1730 which is within circle 1710 but is not within circle 1720 may be assigned to sequencing probe A, area 1740 which is within circle 1720 but is not within circle 1710 may be assigned to sequencing probe B, area 1750 which is within both circle 1710 and circle 1720 may be assigned to sequencing probe A or B with a probability value associated with each of sequencing probe A or B. For example, 40% of droplets with target hybridization signals mapped into data points in area 1750 may correspond to sequencing probe A, while the other 60% of droplets with target hybridization signals mapped into data points in area 1750 may correspond to sequencing probe B.

Figure 18:
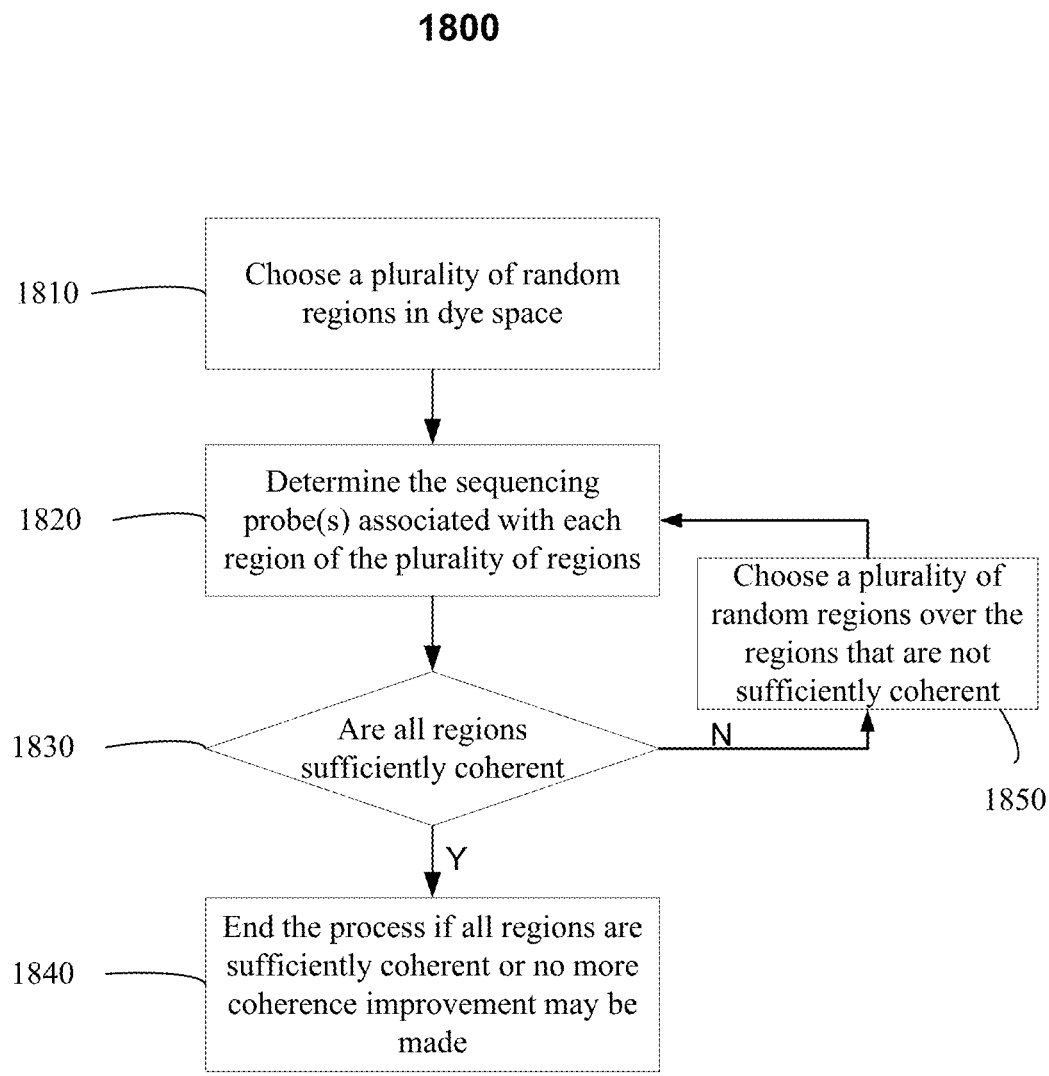
FIG. 18 is a flow chart illustrating a method of selecting a coherent region in a dye space.

FIG. 18 is a flow chart 1800 illustrating a method of selecting coherent regions in a dye space. At block 1810, a plurality of random regions, for example, more than 10000, may be selected. The plurality of regions may have different sizes. At block 1820, a region vector for each of the plurality of regions may be generated and compared with the sequencing probe bit vectors of all sequencing probes to determine the sequencing probe(s) associated with each of the plurality of regions as described above. At block 1830, coherency of the regions can be determined based on, for example, compression ratios of the regions. Regions that can be associated with a sequencing probe with sufficient confidence or are sufficiently coherent are kept. Regions that may not be associated with a sequencing probe with sufficient confidence or are not sufficiently coherent may be discarded. At block 1850, over the regions determined not to be sufficiently coherent, new random regions may be selected, and sequencing probe(s) corresponding to these new random regions may be determined as described above. Regions that can be associated with a sequencing probe with sufficient confidence or are sufficiently coherent are kept. Regions that may not be associated with a sequencing probe with sufficient confidence or are not sufficiently coherent may be discarded and reselected as described above. The above process can be reiterated until no more regions may be selected and assigned to sequencing probe(s) with better confidence or no more coherent regions may be selected at block 1840.

VII. Assay Calling

After regions in the dye space are associated with sequencing probes, a reaction droplet whose target hybridization signal maps to a data point in a region in the dye space can be called to determine the sequencing probe and therefore the complementary sequence in the target nucleic acid, based on the sequencing probe assigned to the region.

Alternatively, when a reaction droplet is read, the detected hybridization signal may be mapped to a data point, a region encompassing the data point may be selected, and the corresponding sequencing probe(s) for the region may be determined as described above and associated with the reaction droplet. In some embodiments, the region with the lowest compression ratio or Shannon entropy may be selected from a plurality of regions that encompass the data point. In some embodiments, multiple regions with compression ratio or Shannon entropy below a threshold value may be selected from the plurality of regions that encompass the data point, and a consensus among the multiple selected regions may determine the corresponding sequencing probe(s) for the data point.

As described above, some regions may have multiple sequencing probes, rather than a single sequencing probe, assigned to it. However, this multi-sequence call can still be used for sequence assembly. This is because the multiple sequencing probes assigned to a same region are likely to be random sequencing probes in the dye space; however, in the sequence space of the target nucleic acid, one sequencing probe of the multiple sequencing probes may fit better than other sequencing probes. Further, if a reference, such as a wild type reference, is available, the reference may be used to determine which sequencing probe is more likely to correspond with a droplet whose hybridization signal maps into a data point in the region.

Figure 19:
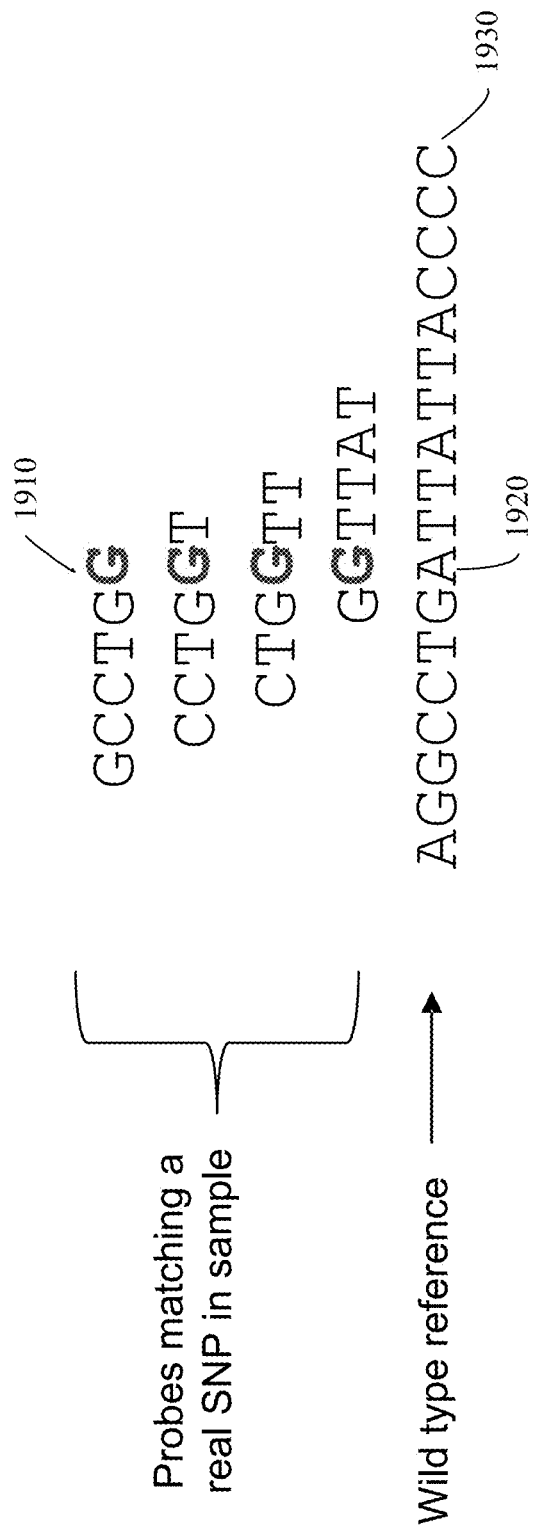
FIG. 19 illustrates an example application of multiple sequencing probes associated with a single region in sequence assembly or variant call (wild-type reference=SEQ ID NO:3).

FIG. 19 illustrates an example application of multiple sequencing probes associated with a single region in sequence assembly or variant call (wild-type reference=SEQ ID NO:3). The sequencing probes can be aligned to each other. As shown, the sequencing probes overlap each other. The overlapping of the sequencing probes can be used to assemble the probes into a consensus sequence for the target nucleic acid. The consensus sequence can be compared to a reference sequence to identify variants. As shown, the highlighted G 1910 differs from the A 1920, and a variant can be identified.

Multiple sequencing probes may be associated with a region in dye space, for example, 30% of the data points in the region corresponds to GCCTGG and 70% of the data points in the region corresponds to AAATTT. Thus, there may be multiple possibilities for which sequencing probe corresponds to a droplet. The multiple sequencing probes associated with the region can still be used for sequence assembly or variant call, e.g., using information about the reference genome in the target genomic region. For example, when a reference sequence, such as a wild type reference sequence 1930, is available, it may be determined that a target data point in the region may correspond to sequencing probe GCCTGG, rather than AAATTT, because the chance that sequencing probe AAATTT may hybridize with a sequence similar to wild type reference sequence 1930 is very low, even when variants are present.

VIII. Example Methods

Figure 20:
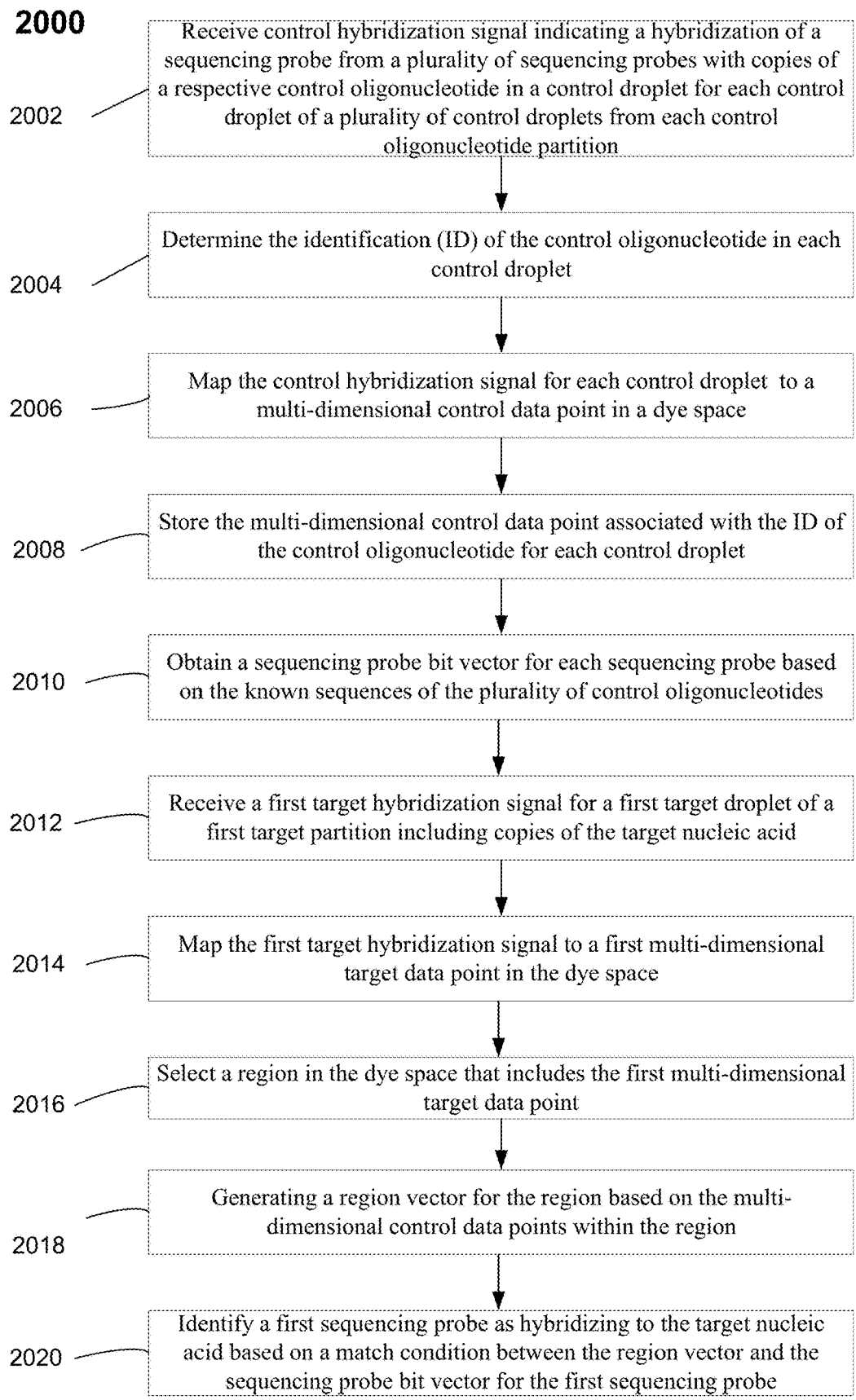
FIG. 20 is a flow chart illustrating a method for determining a sequence of a target nucleic acid.

FIG. 20 is a flow chart 2000 illustrating a method for determining a sequence of a target nucleic acid.

At block 2002, a control hybridization signal indicating a hybridization of a sequencing probe from a plurality of sequencing probes with copies of respective control oligonucleotide in the control droplet is received for each control droplet of a plurality of control droplets from each control partition of a plurality of control partitions. Each control droplet of the plurality of control droplets includes copies of a respective control oligonucleotide of the plurality of control oligonucleotides. Each control oligonucleotide of the plurality of control oligonucleotides has a known sequence and a corresponding identification (ID).

At block 2004, for each control droplet of the plurality of control droplets of each control partition, the identification (ID) of the control oligonucleotide in the control droplet is determined, e.g., as described above with respect to block 1210 of FIG. 12.

At block 2006, the control hybridization signal for each control droplet is mapped to a multi-dimensional control data point in a dye space, e.g., as described above with respect to block 1220 of FIG. 12.

At block 2008, the multi-dimensional control data point associated with the ID of the control oligonucleotide is stored for each control droplet, e.g., as described above with respect to block 1230 of FIG. 12.

At block 2010, for each sequencing probe of the plurality of sequencing probes, a sequencing probe bit vector is obtained based on the known sequences of the plurality of control oligonucleotides, e.g., as described above with respect to block 740 of FIG. 7. Each bit in the sequencing probe bit vector represents a presence or absence of the sequencing probe in a corresponding control oligonucleotide of the plurality of control oligonucleotides, e.g., as shown in FIG. 10.

At block 2012, a first target hybridization signal for a first target droplet of a first target partition including copies of the target nucleic acid is received from, for example, a detector. For example, as described above with respect to blocks 1150 and 1160 of FIG. 11, a partition of the target nucleic acid may be split into a plurality of droplets during the sequencing run, and each droplet can be mixed with a sequencing probe or a control marker probe to form a reaction droplet. The target hybridization signal for each reaction droplet may be detected by a detector and sent to a computer system for processing.

At block 2014, the first target hybridization signal can be mapped to a first multi-dimensional target data point in the dye space, in a way similar to the mapping of control hybridization signals described above with respect to block 630 of FIG. 6 and block 1220 of FIG. 12.

At block 2016, a region in the dye space that includes the first multi-dimensional target data point is selected, e.g., as described above with respect to block 1410 of FIG. 14 and FIG. 18.

At block 2018, a region vector for the region is generated, e.g., as described above with respect to block 1420 of FIG. 14. Each value in the region vector represents a contribution of any multi-dimensional control data points that are within the region and that have the ID of the corresponding control oligonucleotide as shown in, for example, FIGS. 15B and 16.

At block 2020, a first sequencing probe is identified as hybridizing to the target nucleic acid based on a match condition between the region vector and the sequencing probe bit vector for the first sequencing probe, e.g., as described above with respect to blocks 1430 and 1440 of FIG. 14.

Figure 21:
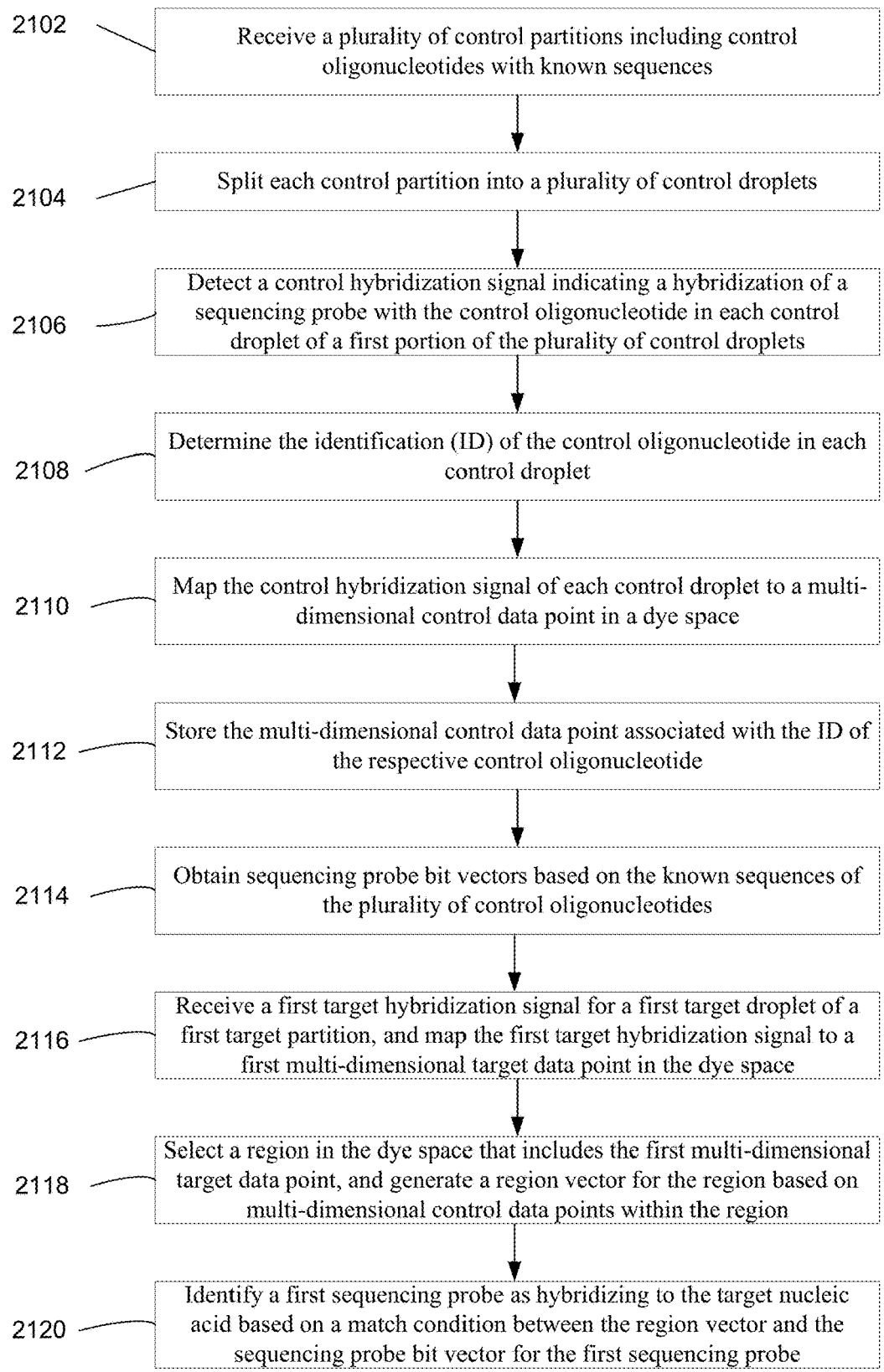
FIG. 21 is a flow chart illustrating another method for determining a sequence of a target nucleic acid.

FIG. 21 is a flow chart 2100 illustrating another method for determining a sequence of a target nucleic acid.

At block 2102, an SBH system receives a plurality of control partitions, e.g., as described above with respect to block 1120 of FIG. 11. Each control partition of the plurality of control partitions may include copies of a respective control oligonucleotide from a plurality of control oligonucleotides, and each control oligonucleotide of the plurality of control oligonucleotides has a known sequence and a corresponding identification (ID).

At block 2104, each control partition of the plurality of control partitions is split into a plurality of control droplets, e.g., as described above with respect to block 1150 of FIG. 11, where each control droplet includes a plurality of copies of the control oligonucleotide for the control partition.

At block 2106, a control hybridization signal indicating a hybridization of a sequencing probe from a plurality of sequencing probes with copies of the control oligonucleotide in the control droplet can be detected for each control droplet in a first portion of the plurality of control droplets, e.g., as described above with respect to block 1160 of FIG. 11 and block 2002 of FIG. 20.

At block 2108, the ID of the control oligonucleotide in each control droplet may be determined, e.g., as described above with respect to block 1210 of FIG. 12 and block 2004 of FIG. 20.

At block 2110, the control hybridization signal for each control droplet in the first portion of the plurality of control droplets can be mapped to a multi-dimensional control data point in a dye space, e.g., as described above with respect to block 1220 of FIG. 12 and block 2006 of FIG. 20.

At block 2112, the multi-dimensional control data point associated with the ID of the respective control oligonucleotide can be stored, e.g., as described above with respect to block 1230 of FIG. 12 and block 2008 of FIG. 20.

At block 2114, a sequencing probe bit vector based on the known sequences of the plurality of control oligonucleotides can be received or otherwise obtained, e.g., as described above with respect to block 740 of FIG. 7 and block 2010 of FIG. 20. Each bit in the sequencing probe bit vector represents a presence or absence of the sequencing probe in a corresponding control oligonucleotide of the plurality of control oligonucleotides, as shown in, for example, FIG. 10.

At block 2116, a first target hybridization signal for a first target droplet of a first target partition including copies of the target nucleic acid is received from, for example, a detector, as described above with respect to blocks 1150 and 1160 of FIG. 11 and block 2012 of FIG. 20. The first target hybridization signal can be mapped to a first multi-dimensional target data point in the dye space, e.g., as described above with respect to block 2014 of FIG. 20.

At block 2118, a region in the dye space that includes the first multi-dimensional target data point is selected, e.g., as described above with respect to block 1410 of FIG. 14, FIG. 18, and block 2016 of FIG. 20. A region vector for the region can be generated, e.g., as described above with respect to block 1420 of FIG. 14 and block 2018 of FIG. 20. Each value in the region vector represents a contribution of any multi-dimensional control data points that are within the region and that have the ID of the corresponding control oligonucleotide, as shown in, for example, FIGS. 15B and 16.

At block 2120, a first sequencing probe is identified as hybridizing to the target nucleic acid based on a match condition between the region vector and a first sequencing probe bit vector for the first sequencing probe, e.g., as described above with respect to blocks 640 and 650 of FIG. 6, blocks 1430 and 1440 of FIG. 14, and block 2020 of FIG. 20.

Alternatively, as described above with respect to FIG. 6, a region vector may be created for each region or each coherent region in the dye space. The region vector can be compared against the sequencing probe bit vector for each sequencing probe to determine one or more sequencing probes corresponding to each region. After the sequencing run or during the sequencing run, target hybridization signals of target droplets including copies of the target nucleic acids may be mapped to multi-dimensional target data points in the dye space. For each target data point in the dye space, one or more sequencing probes may be associated with the target data point based on the one or more sequencing probes corresponding to the region that the target data point falls into in the dye space.

IX. Example Results

This section describes simulation results using the above described methods in making assay calls.

Figure 22A:
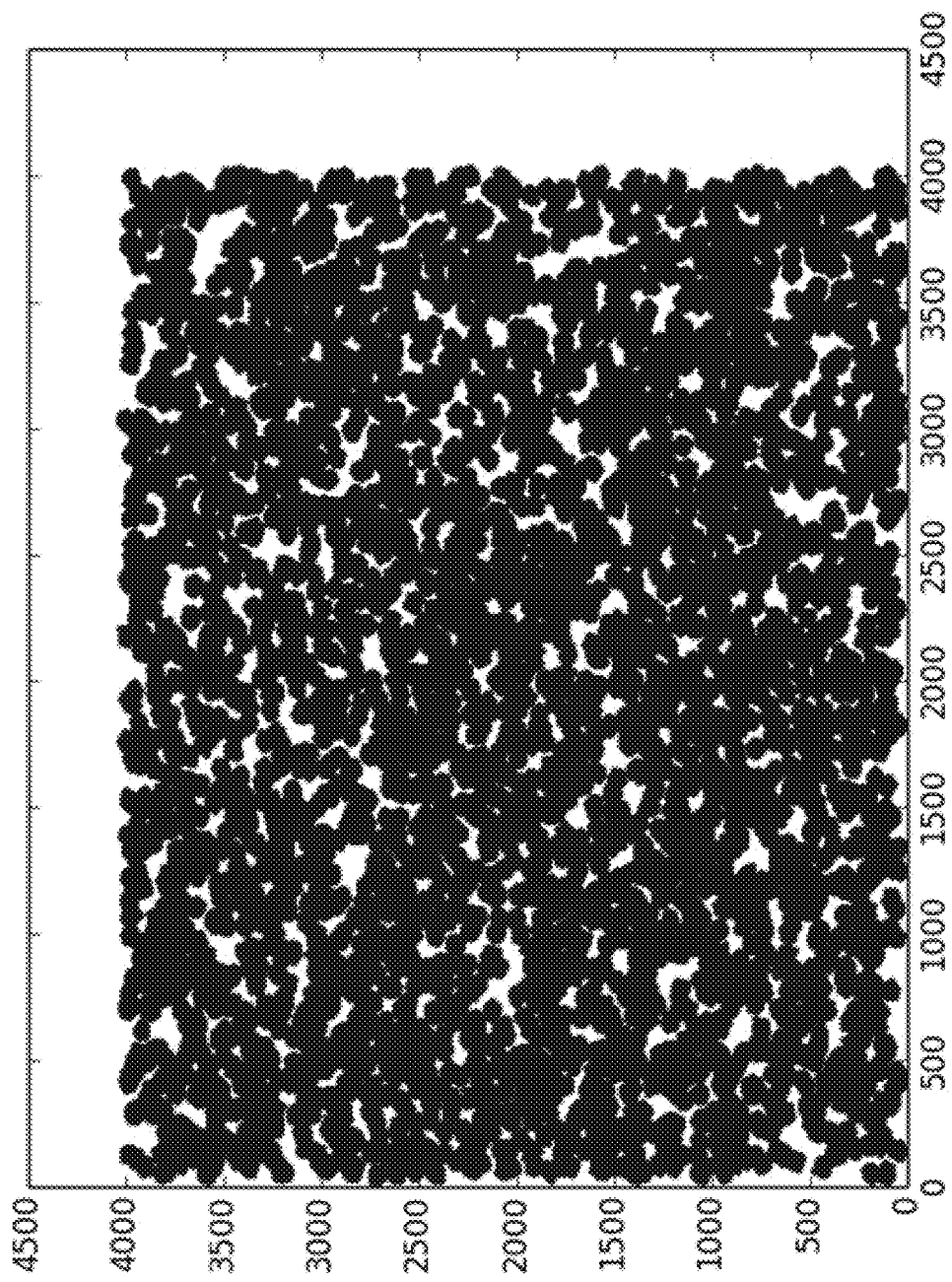
FIGS. 22A-22C illustrate a set of example data points densely packed in a two-dimensional space mapped from target hybridization signals.
Figures 22B, 22C:
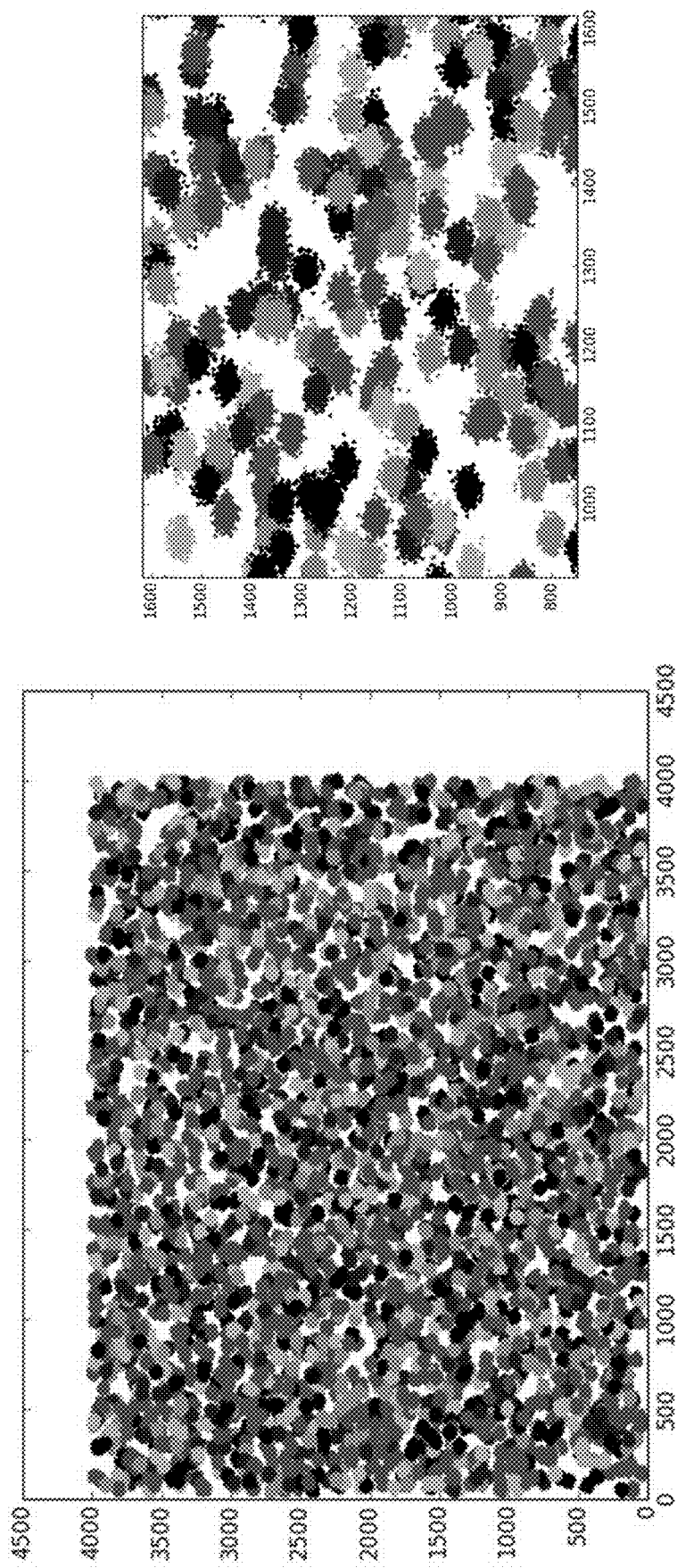

In a first example, data points in a two-dimensional space mapped from target hybridization signals are shown in FIGS. 22A-22C, wherein 4096 clusters are shown in the same color in FIG. 22A, and in different colors in FIG. 22B. FIG. 22C is a zoom-in view of FIG. 22B. It can be seen from FIGS. 22A-22C that the data points are densely packed, the centroids of the clusters are randomly located rather than on a grid, and there are many overlapping clusters. Thus, it is very difficult to make a correct call for many data points in FIGS. 22A-22C. Using the methods described in the present disclosure, 1000 randomly selected regions each with a radius of 10 are correctly associated with their corresponding sequencing probes, wherein the association is deemed correct for a region if more than 90% of the droplets falling into the region can be correctly identified using the associated sequencing probe(s) for the region. 97% of droplets with hybridization signals mapped into data points in the 1000 regions are correctly called. Even if it is assumed that 40% of the control hybridization signals are misidentified, the method can still correctly identify 99% of the 1000 regions and correctly call 92% of all droplets within the 1000 regions. For the 3% or 8% miscalled droplets, 90% of them can be correctly called by choosing a different region.

Figure 22D:
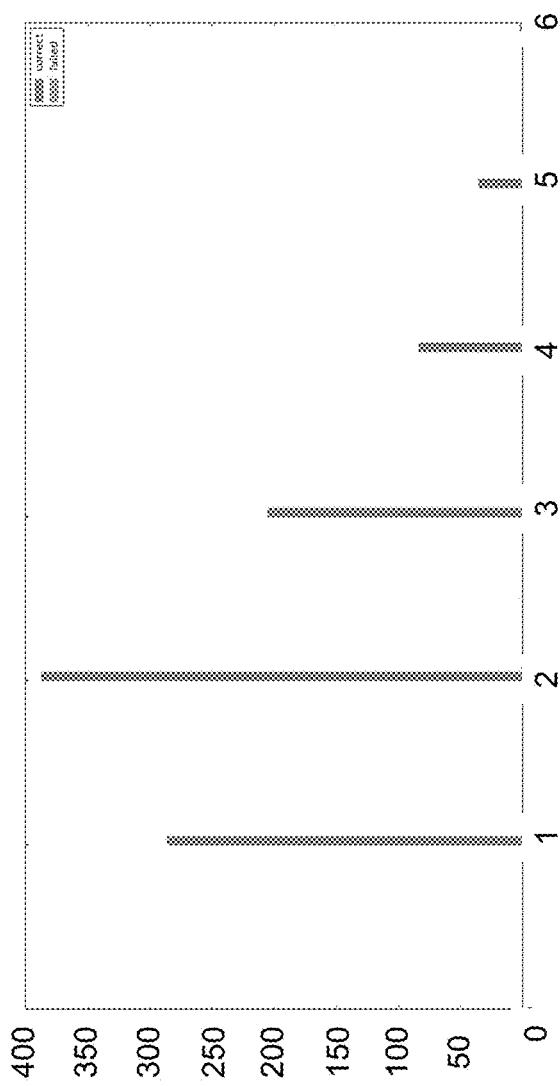
FIG. 22D illustrates a result of cluster overlapping and errors in associating a region with its corresponding sequencing probes using the example data points shown in FIGS. 22A-22C.

FIG. 22D illustrates a result of cluster overlapping and errors in associating a region with its corresponding sequencing probes, using example data points shown in FIGS. 22A-22C. In FIG. 22D, x-axis represents the number of sequencing probes falling within a random circular region of radius 10, y-axis represents the number of regions with one or more sequencing probes. The blue bars represent the number of regions that are correctly associated with one or more sequencing probes, and the green bars represent the number of regions that are not correctly associated with one or more sequencing probes. FIG. 22D shows that many random circular regions have more than one sequencing probes falling within each circular region, and all 1000 randomly selected regions are correctly associated with their corresponding sequencing probes. Thus, even in a densely packed multi-dimensional space where a majority of regions have more than one associated probes, the method described herein is still very robust.

Figure 22E:
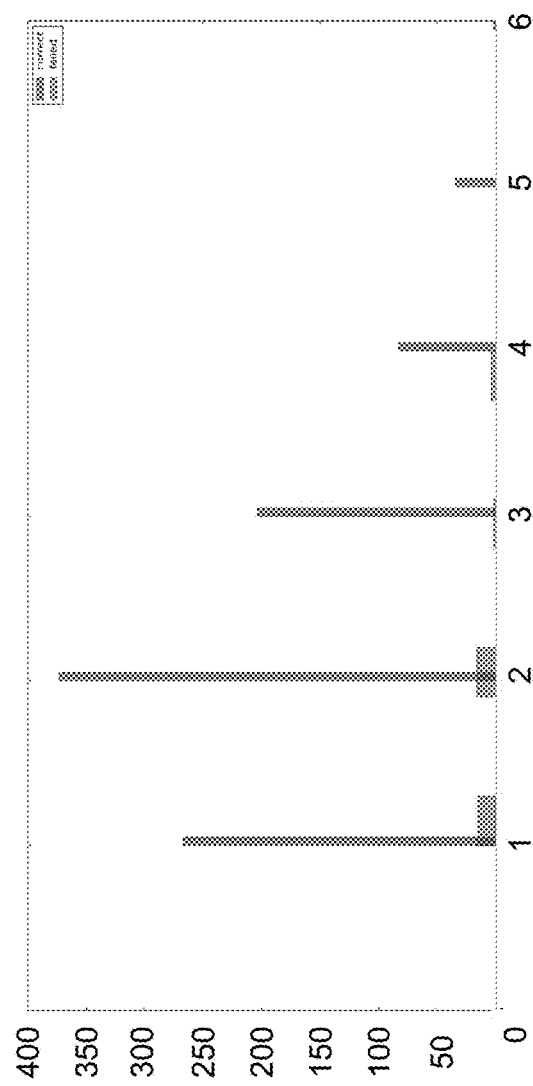
FIG. 22E illustrates a result of cluster overlapping and errors in associating a region with its corresponding sequencing probes using the example data points shown in FIGS. 22A-22C, with 40% of noise added.

FIG. 22E illustrates a result of cluster overlapping and errors in associating a region with its corresponding sequencing probes using the example data points shown in FIGS. 22A-22C, with 40% of noise added. FIG. 22E shows that most of the 1000 randomly selected regions are correctly associated with their corresponding sequencing probes even with 40% of noise added.

Figure 23A:
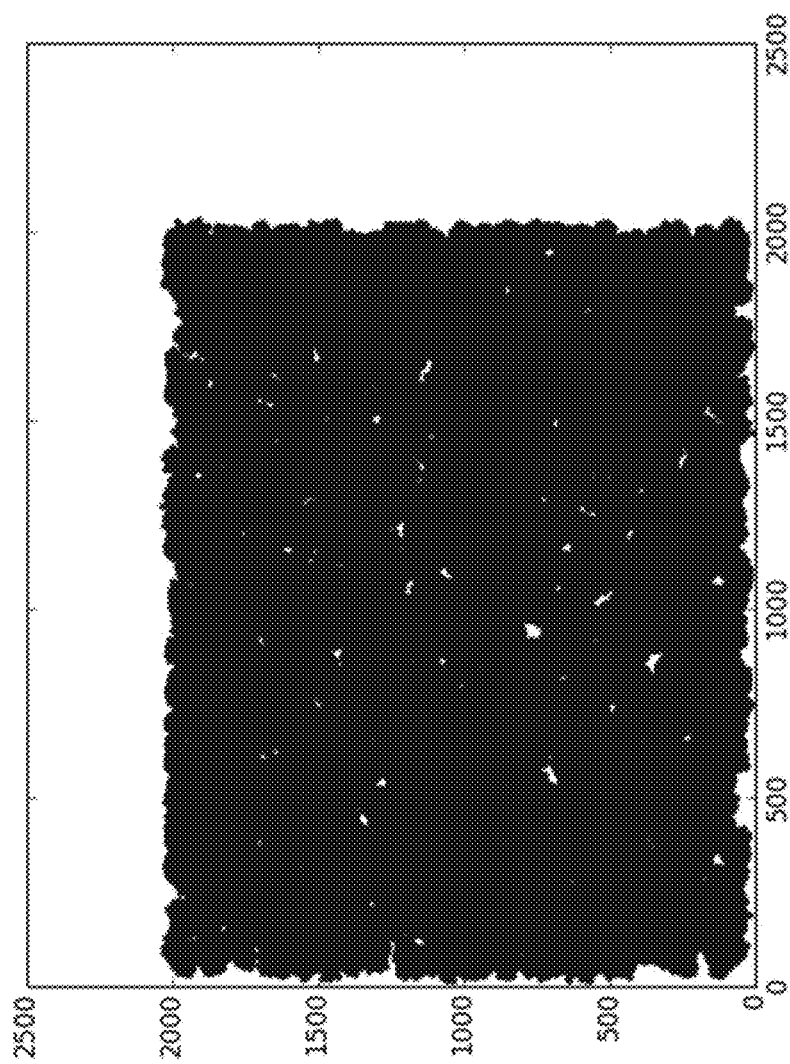
FIGS. 23A-23C illustrate another set of example data points densely packed in a two-dimensional space mapped from target hybridization signals.
Figure 23C:
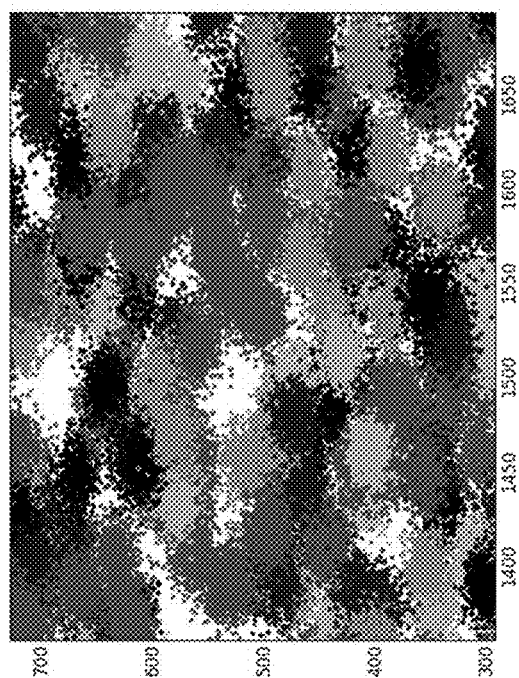
Figure 23B:
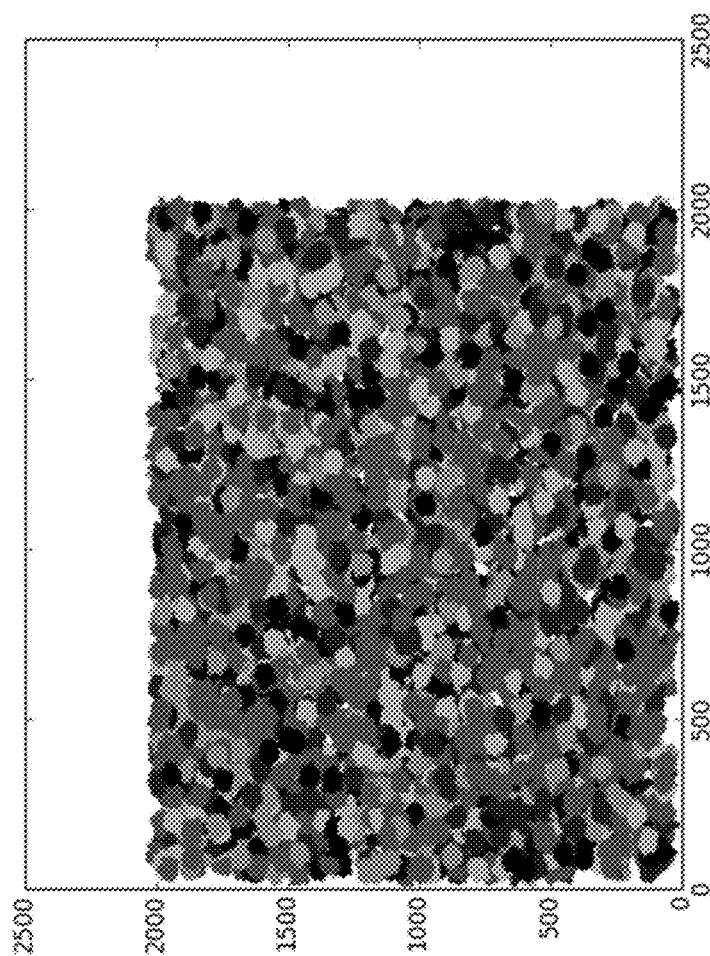

FIGS. 23A-23C illustrate another example of data points densely packed in a two-dimensional space mapped from target hybridization signals. FIG. 23A illustrates data points of 4096 clusters in the same color. FIG. 23B illustrates data points of 4096 clusters in different color. FIG. 23C is a zoom-in view of FIG. 23B. In the example shown in FIGS. 23A-23C, where data points are even more densely packed, 99% of 1000 randomly selected regions each with a radius of 5 are correctly associated with their corresponding sequencing probes using the methods described in the present disclosure. 83% of droplets with hybridization signals mapped into data points in the 1000 regions are correctly called. For the 17% miscalled droplets, 85% of them can be correctly called by choosing a different region.

Figure 23D:
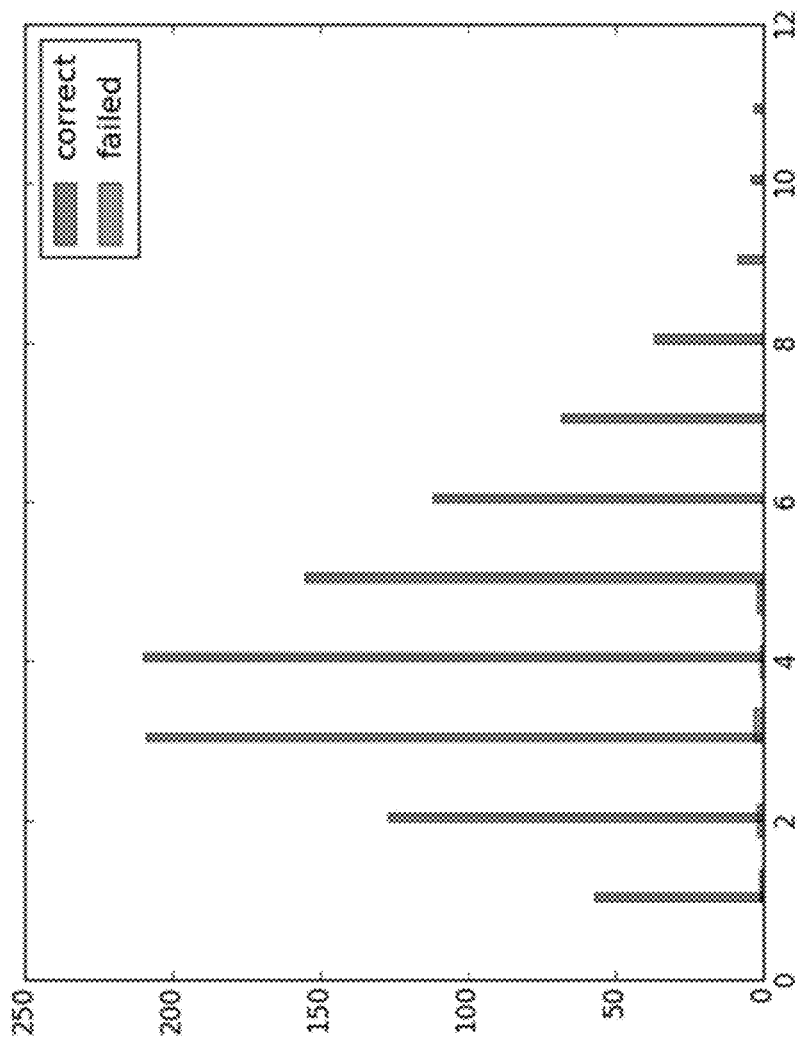
FIG. 23D illustrates a result of cluster overlapping and errors in associating a region with its corresponding sequencing probes using the example data points shown in FIGS. 23A-23C.

FIG. 23D illustrates a result of cluster overlapping and errors in associating a region with its corresponding sequencing probes, for the example data points shown in FIGS. 23A-23C. In FIG. 23D, x-axis represents the number of sequencing probes falling within a random circular region of radius 5, y-axis represents the number of regions with one or more sequencing probes. The blue bars represent the number of regions that are correctly associated with one or more sequencing probes, and the green bars represent the number of regions that are not correctly associated with one or more sequencing probes. FIG. 23D shows that many random circular regions have more than one sequencing probe falling within each circular region, and 99% of all 1000 randomly selected regions are correctly associated with their corresponding sequencing probes.

X. Improvement Over Conventional Methods

As described above with respect to FIGS. 3-5, if no error or noise is present, the detected hybridization signal of a reaction droplet would be mapped to a coordinate in the dye space that falls into the cluster for the sequencing probe in each reaction droplet. However, due to imperfections in the assaying, data points in the dye space may not cluster around the ideal grid of, for example, 4096 centroids, and the dye space may be densely packed and the clusters may overlap without a clear separation. Thus, it may be very difficult, if not impossible, to correctly cluster the densely packed or overlapped data points in dye space, such as the data points shown in FIGS. 22A-22C and 23A-23C.

Furthermore, even if data points can be properly clustered in a dye space, the data points may include many irregularities from an ideal or designed grid, such as, for example, centroids may be missing or shifted to neighboring columns. As such, the actual dye space location or centroid of the cluster for a sequencing probe may be different from the designed location in the designed grid, and therefore an assay calling based on the designed location in the dye space for the sequencing probe may provide false results. Thus, using a conventional clustering method based only on dye space data points of reaction droplets from target nucleic acid partitions, it may be impossible to correctly identify the sequencing probe associated with each data point for data points shown in FIGS. 22A-22C and 23A-23C.

Embodiments described in the present disclosure do not depend on the designed grid for mapping between dye space locations and sequencing probes, and do not require a-priori knowledge of the location of the cluster for a sequencing probe in the dye space. Even if the mapping between dye space locations and sequencing probes is totally random, embodiments may still properly identify the sequencing probe associated with a droplet based on its mapped data point in the dye space. This is at least because the densely packed identity space is mapped into a sparsely packed identity space such that clustering is relatively easy, and the location of a sequencing probe in the identity space is identified during or after the actual sequencing run using control oligonucleotides with known sequences and correctly identifiable unique IDs.

XI. Computer System

Figure 24:
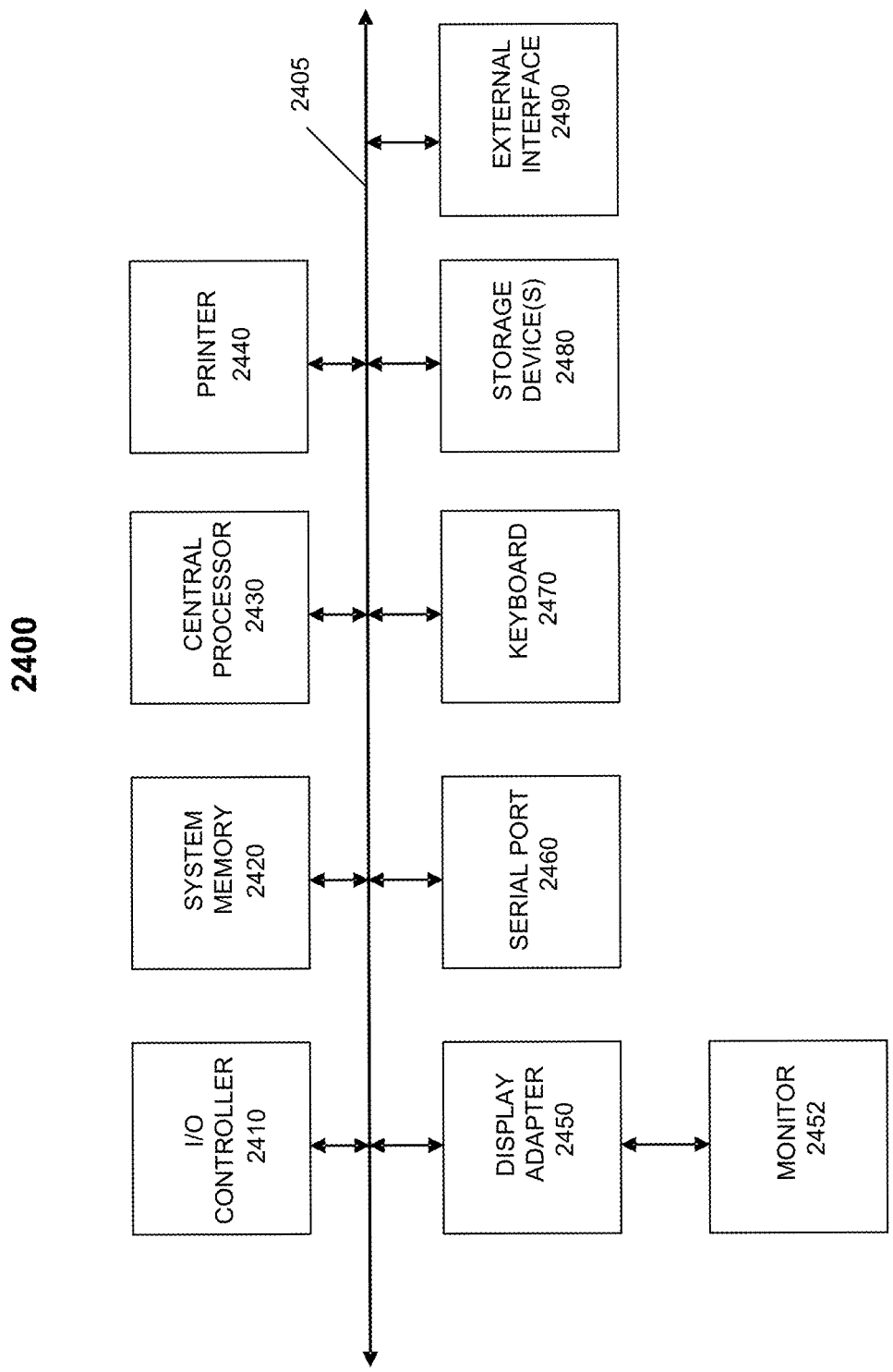
FIG. 24 illustrates a computer system on which embodiments of the present disclosure may be performed.

Any of the computer systems mentioned herein may utilize any suitable number of subsystems. Examples of such subsystems are shown in FIG. 24 in computer system 2400. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 24 are interconnected via a system bus 2405. Additional subsystems such as a printer 2440, keyboard 2470, storage device(s) 2480, monitor 2452, which is coupled to display adapter 2450, and others are shown. Peripherals and input/output (I/O) devices, which couple to I/O controller 2410, can be connected to the computer system by any number of means known in the art, such as serial port 2460. For example, serial port 2460 or external interface 2490 (e.g., Ethernet, Wi-Fi, etc.) can be used to connect computer system 2400 to a wide area network such as the Internet, a mouse input device, or a scanner. The interconnection via system bus 2405 allows central processor 2430 to communicate with each subsystem and to control the execution of instructions from system memory 2420 or the storage device(s) 2480 (e.g., a fixed disk), as well as the exchange of information between subsystems. System memory 2420 and/or storage device(s) 2480 may embody a computer readable medium. Any of the values mentioned herein can be output from one component to another component and can be output to the user.

A computer system can include a plurality of the same components or subsystems, e.g., connected together by external interface 2490 or by an internal interface. In some embodiments, computer systems, subsystems, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g., an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or network. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g., a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a," "an" or "the" is intended to mean "one or more" unless specifically indicated to the contrary. The use of "or" is intended to mean an "inclusive or," and not an "exclusive or" unless specifically indicated to the contrary.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes. None is admitted to be prior art.

What is claimed is:

1. A method of sequencing a target nucleic acid, the method comprising:
receiving a plurality of sequencing probes, the plurality of sequencing probes including $4^N$ sequencing probes, wherein each of the $4^N$ sequencing probes includes N nucleotides;
receiving a plurality of control partitions, wherein each control partition of the plurality of control partitions includes copies of a respective control oligonucleotide from a plurality of control oligonucleotides, wherein the plurality of control oligonucleotides are configured such that each of the $4^N$ sequencing probes is configured to hybridize with at least one control oligonucleotide in the plurality of control oligonucleotides, and wherein each control oligonucleotide of the plurality of control oligonucleotides has a known sequence and a corresponding identification sequence that indicates an identification (ID) of the control oligonucleotide;
for each control partition of the plurality of control partitions:
splitting the control partition into a plurality of control droplets, each control droplet including a plurality of copies of the control oligonucleotide for the control partition; and
for each control droplet of a first portion of the plurality of control droplets:
detecting a control hybridization signal indicating a hybridization of a sequencing probe from the plurality of sequencing probes with copies of the control oligonucleotide in the control droplet;
determining the ID of the control oligonucleotide in the control droplet;
mapping the control hybridization signal to a multi-dimensional control data point in a dye space; and
storing the multi-dimensional control data point associated with the ID of the respective control oligonucleotide;
for each sequencing probe of the plurality of sequencing probes:
receiving a sequencing probe bit vector based on the known sequences of the plurality of control oligonucleotides, wherein each bit in the sequencing probe bit vector represents a presence or absence of the sequencing probe in a corresponding control oligonucleotide of the plurality of control oligonucleotides;
receiving of a plurality of target partitions including copies of the target nucleic acid;
receiving a first target hybridization signal for a first target droplet of a first target partition of the plurality of target partitions;
mapping the first target hybridization signal to a first multi-dimensional target data point in the dye space;
selecting a region in the dye space that includes the first multi-dimensional target data point;
generating a region vector for the region, wherein each value in the region vector represents a contribution of multi-dimensional control data points that are within the region and that have the ID of the corresponding control oligonucleotide;
converting the region vector to a region bit vector based on a threshold value;
identifying a first sequencing probe associated with the region based on a match condition between the region bit vector and a first sequencing probe bit vector for the first sequencing probe; and
determining a section in the sequence of the target nucleic acid as corresponding to the identified first sequencing probe.

2. The method of claim 1, wherein the control oligonucleotide in each control partition includes a control marker from a plurality of control markers as the corresponding ID of the control oligonucleotide, the plurality of control markers being detectable by a plurality of control marker probes.

3. The method of claim 2, wherein each of the plurality of control marker probes includes a different number of nucleotides from any of the plurality of sequencing probes.

4. The method of claim 2, wherein a second portion of the plurality of control droplets each includes a control marker probe.

5. The method of claim 4, wherein a number of control droplets of the second portion of the plurality of control droplets is less than 20% of a number of control droplets of the plurality of control droplets.

6. The method of claim 1, wherein a number of base pairs in each control oligonucleotide is less than 20% of a number of sequencing probes of the plurality of sequencing probes.

7. The method of claim 1, wherein a number of control partitions of the plurality of control partitions is less than 20% of a total number of partitions of the plurality of target partitions and the plurality of control partitions.

* * * * *